(12) United States Patent
Davidson

(10) Patent No.: US 9,795,400 B2
(45) Date of Patent: Oct. 24, 2017

(54) GALVANICALLY ASSISTED ATTACHMENT OF MEDICAL DEVICES TO THROMBUS

(71) Applicant: COVIDIEN LP, Mansfield, MA (US)

(72) Inventor: James Davidson, San Juan Capistrano, CA (US)

(73) Assignee: Covidien LP, Mansfield, MA (US)

( * ) Notice: Subject to any disclaimer, the term of this patent is extended or adjusted under 35 U.S.C. 154(b) by 334 days.

(21) Appl. No.: 14/541,094

(22) Filed: Nov. 13, 2014

(65) Prior Publication Data
US 2015/0133990 A1   May 14, 2015

Related U.S. Application Data

(60) Provisional application No. 61/903,518, filed on Nov. 13, 2013.

(51) Int. Cl.
*A61M 29/00* (2006.01)
*A61B 17/221* (2006.01)
(Continued)

(52) U.S. Cl.
CPC .............. *A61B 17/221* (2013.01); *A61F 2/01* (2013.01); *A61N 1/378* (2013.01);
(Continued)

(58) Field of Classification Search
CPC .......... A61B 17/221; A61B 2017/2212; A61B 2017/2215; A61B 2017/2217;
(Continued)

(56) References Cited

U.S. PATENT DOCUMENTS 5,904,651 A   5/1999  Swanson et al.
6,015,424 A   1/2000  Rosenbluth et al.
(Continued)

FOREIGN PATENT DOCUMENTS

CN    103153214 A   6/2013
WO    WO-2009/105710 A1   8/2009
(Continued)

OTHER PUBLICATIONS

Duncan, et al., "On the treatment of aneurism by electrolysis: with an account of an investigation into the action of galvanism on blood and on albuminous fluids", Medico-Chir Soc Edinb Med J, 13, 1867, pp. 101-120.
(Continued)

*Primary Examiner* — Jonathan Miles
(74) *Attorney, Agent, or Firm* — Mark Kertz

(57) ABSTRACT

A medical device configured to perform an endovascular therapy can include an elongate manipulation member and an intervention member. The elongate manipulation member can include a distal end portion. The intervention member can include a proximal end portion and a mesh. The proximal end portion can be coupled with the distal end portion of the elongate manipulation member. The mesh can have a plurality of cells in a tubular configuration and being compressible to a collapsed configuration for delivery to an endovascular treatment site through a catheter and being self-expandable from the collapsed configuration to an expanded configuration. The mesh can include an anodic metal and a cathodic metal. The anodic metal and the cathodic metal can each form a fraction of a total surface area of the mesh.

15 Claims, 20 Drawing Sheets

(51) Int. Cl.
*A61F 2/01* (2006.01)
*A61N 1/378* (2006.01)
*A61B 17/22* (2006.01)
*A61B 17/00* (2006.01)

(52) U.S. Cl.
CPC ............ *A61B 2017/00831* (2013.01); *A61B 2017/00929* (2013.01); *A61B 2017/22001* (2013.01); *A61B 2017/2215* (2013.01); *A61B 2017/22034* (2013.01); *A61B 2017/22094* (2013.01); *A61F 2002/016* (2013.01); *A61F 2230/0023* (2013.01); *A61F 2250/0043* (2013.01)

(58) Field of Classification Search
CPC ........ A61B 17/22031; A61B 17/22032; A61B 2017/22034; A61B 2017/22035; A61F 2/01; A61F 2/013; A61F 2002/015; A61F 2002/016; A61F 2002/018; A61F 2/07; A61F 2002/072; A61F 2002/075; A61F 2002/077; A61F 2/82; A61F 2002/821; A61F 2002/823; A61F 2002/825; A61F 2002/826; A61F 2002/828; A61F 2/856; A61F 2/86; A61F 2/88; A61F 2/885; A61F 2/89; A61F 2/90; A61F 2/91; A61F 2/915; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2/94; A61F 2/945
See application file for complete search history.

(56) References Cited

U.S. PATENT DOCUMENTS

| | | | |
|---|---|---|---|
| 6,416,530 B2 | 7/2002 | DeVries et al. | |
| 6,658,288 B1 | 12/2003 | Hayashi | |
| 7,300,458 B2 | 11/2007 | Henkes et al. | |
| 7,458,974 B1 | 12/2008 | Hayashi et al. | |
| 8,016,853 B2 | 9/2011 | Griffen et al. | |
| 8,052,744 B2* | 11/2011 | Girton ................ | A61L 31/146 623/1.39 |
| 8,114,148 B2 | 2/2012 | Atanasoska et al. | |
| 8,236,046 B2 | 8/2012 | Weber | |
| 8,556,927 B2 | 10/2013 | Dehnad | |
| 8,668,732 B2 | 3/2014 | Scheuermann et al. | |
| 8,715,339 B2 | 5/2014 | Atanasoska et al. | |
| 2002/0082679 A1* | 6/2002 | Sirhan ................ | A61F 2/91 623/1.15 |
| 2002/0120297 A1 | 8/2002 | Shadduck | |
| 2003/0217794 A1 | 11/2003 | Boylan et al. | |
| 2005/0119723 A1 | 6/2005 | Peacock | |
| 2005/0178584 A1* | 8/2005 | Wang ................ | A61L 31/14 174/256 |
| 2006/0122694 A1* | 6/2006 | Stinson ................ | A61F 2/91 623/1.34 |
| 2006/0271169 A1* | 11/2006 | Lye ................ | A61L 31/082 623/1.39 |
| 2006/0293706 A1 | 12/2006 | Shimon et al. | |
| 2007/0270942 A1 | 11/2007 | Thomas | |
| 2008/0058919 A1* | 3/2008 | Kramer-Brown ....... | A61L 31/08 623/1.34 |
| 2008/0071350 A1* | 3/2008 | Stinson ................ | A61F 2/91 623/1.15 |
| 2008/0082162 A1* | 4/2008 | Boismier ............. | A61F 2/91 623/1.38 |
| 2008/0262489 A1 | 10/2008 | Steinke | |
| 2009/0149947 A1* | 6/2009 | Frohwitter ........... | A61F 2/86 623/1.42 |
| 2009/0248060 A1 | 10/2009 | Schneider et al. | |
| 2010/0008970 A1 | 1/2010 | O'Brien et al. | |
| 2010/0145380 A1 | 6/2010 | Quandt et al. | |
| 2011/0060212 A1 | 3/2011 | Slee et al. | |
| 2011/0160763 A1 | 6/2011 | Ferrera et al. | |
| 2011/0238153 A1* | 9/2011 | Atanasoska ........... | A61F 2/91 623/1.15 |
| 2011/0282428 A1* | 11/2011 | Meyer ................ | A61F 2/915 623/1.15 |
| 2011/0301594 A1 | 12/2011 | Orion | |
| 2012/0083868 A1 | 4/2012 | Shrivastava et al. | |
| 2013/0066359 A1 | 3/2013 | Murphy et al. | |
| 2013/0072960 A1 | 3/2013 | Schneider et al. | |
| 2013/0096606 A1 | 4/2013 | Bruchman et al. | |
| 2014/0018844 A1 | 1/2014 | Dehnad | |
| 2014/0031858 A1 | 1/2014 | Bhagchandani et al. | |
| 2014/0194911 A1 | 7/2014 | Johnson et al. | |
| 2014/0194919 A1 | 7/2014 | Losordo et al. | |
| 2015/0080937 A1 | 3/2015 | Davidson | |
| 2015/0297803 A1* | 10/2015 | Pulugurtha .......... | A61L 31/148 623/1.22 |

FOREIGN PATENT DOCUMENTS

| | | |
|---|---|---|
| WO | WO-2013/071173 A1 | 5/2013 |
| WO | WO-2014/041428 A2 | 3/2014 |

OTHER PUBLICATIONS

Piton, et.al., "Vascular thrombus induced by direct electric current", Neuroradiology, 16, 1, 1978, pp. 385-388.

Schumacher, et.al., "A ferret model of electrical-induction of arterial thrombosis that is sensitive to aspirin", J. Pharm. & Tox Methods, 35, 1, 1996, pp. 3-10.

Shih, "Galvanic current induced heterogeneous structures on stainless steel wire", Cor. Sci., 47, 8, 2005, pp. 2199-2212.

Siddique, et al., "Treatment of aneurysms with wires and electricity: a historical overview", J. Neurosurg., 99, 2003, pp. 1102-1107.

* cited by examiner

GALVANICALLY ASSISTED ATTACHMENT OF MEDICAL DEVICES TO THROMBUS

CROSS-REFERENCE TO RELATED APPLICATION GROUND

This application claims the priority benefit of U.S. Provisional Patent Application No. 61/903,518, filed Nov. 13, 2013, titled GALVANICALLY ENHANCED MEDICAL DEVICES AND METHODS, the entirety of which is incorporated by reference herein.

BACKGROUND

Blood vessels can become partially or completely occluded by emboli, e.g., thrombi, thereby impeding or disrupting the flow of blood therethrough. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

An aspect of at least some of the embodiments disclosed herein involves the recognition that a galvanically induced electrical charge can assist attachment of preexisting thrombotic material to a mechanical thrombus-retrieval device and, thereby, improve a likelihood of successful thrombus capture and retrieval from a patient's body. The electrical charge generated by a galvanic couple can cause or increase adhesion between one or more of the metals in the galvanic couple and the thrombotic material.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 8, 22, 32, 40, 47, 56, 65, or 69. The other clauses can be presented in a similar manner.

1. A medical device configured to perform an endovascular therapy, the device comprising:
   an elongate manipulation member comprising a distal end portion; and
   an intervention member comprising a proximal end portion and a mesh, the proximal end portion being coupled with the distal end portion of the elongate manipulation member, the mesh having a plurality of cells in a tubular configuration and being compressible to a collapsed configuration for delivery to an endovascular treatment site through a catheter and being self-expandable from the collapsed configuration to an expanded configuration, and the mesh comprising an anodic metal and a cathodic metal, and the anodic metal and the cathodic metal each forming a fraction of a total surface area of the mesh.

2. The medical device of Clause 1, wherein the fraction of the surface area formed by the anodic metal is located primarily at an internal aspect of the mesh.

3. The medical device of Clause 1, wherein less than 50% of the surface area formed by the anodic metal is located at an external surface of the mesh.

4. The medical device of Clause 1, wherein 35% to 85% of the surface area of the mesh is formed by the anodic metal.

5. The medical device of Clause 1, wherein an outwardly facing surface of the mesh is formed substantially only by the cathodic metal.

6. The medical device of Clause 1, wherein the fraction of the surface area formed by the anodic metal comprises a plurality of discrete portions of the anodic metal.

7. The medical device of Clause 1, wherein the fraction of the surface area formed by the anodic metal is contiguous.

8. The medical device of Clause 1, wherein an engagement portion of the surface area is configured to engage an interior surface of a catheter during delivery of the medical device through a lumen of the catheter, and an average coefficient of friction of the engagement portion is less than an average coefficient of friction of the surface area excluding the engagement portion.

9. The medical device of Clause 1, wherein an engagement portion of the surface area is configured to engage an interior surface of a catheter during delivery of the medical device through a lumen of the catheter, and substantially none of the engagement portion is formed by the anodic metal.

10. The medical device of Clause 1, wherein the anodic metal is in direct contact with the cathodic metal.

11. The medical device of Clause 1, wherein at least a portion of the anodic metal has a thickness of at least 2 μm.

12. The medical device of Clause 1, wherein the anodic metal comprises magnesium and the cathodic metal comprises nickel and titanium.

13. The medical device of Clause 1, wherein the mesh is rolled in the collapsed configuration such that a first portion and a second portion of the mesh are overlapped in at least one radial direction with a surface area of the first portion contacting a surface area of the second portion, and each of the surface area of the first portion and the surface area of the second portion comprises substantially no anodic metal.

14. The medical device of Clause 1, further comprising a temporary cover material that encapsulates at least a portion of the anodic metal.

15. The medical device of Clause 14, wherein the temporary cover material is erodible, dissolvable, degradable or absorbable in vivo.

16. The medical device of Clause 15, wherein the temporary cover material encapsulates substantially all of the anodic metal.

17. A medical device configured to perform an endovascular therapy, the device comprising:
   an elongate manipulation member comprising a distal end portion; and
   an intervention member comprising a proximal end portion and a mesh, the proximal end portion being coupled with the distal end portion of the elongate manipulation member, the mesh having a plurality of cells in a tubular configuration and being compressible to a collapsed configuration for delivery to an endovascular treatment site through a catheter and being self-expandable from the collapsed configuration to an expanded configuration, and the mesh comprising means for galvanically assisting internal attachment of the mesh to thrombus.

18. The medical device of Clause 17, wherein the means for galvanically assisting attachment of the mesh to thrombus comprises an anodic metal and a cathodic metal.

19. The medical device of Clause 17, wherein the anodic metal comprises magnesium and the cathodic metal comprises nickel and titanium.

20. A method for performing an endovascular therapy, comprising:

identifying a blood vessel in which blood flow is impeded by thrombus;

inserting a medical device into the blood vessel, the medical device comprising:

an elongate manipulation member comprising a distal end portion; and an intervention member comprising a proximal end portion and a mesh, the proximal end portion being coupled with the distal end portion of the elongate manipulation member, the mesh having a plurality of cells in a tubular configuration and being compressible to a collapsed configuration for delivery to an endovascular treatment site through a catheter and being self-expandable from the collapsed configuration to an expanded configuration, and the mesh comprising at least one galvanic cell;

expanding the mesh into at least a portion of the thrombus;

galvanically assisting attachment of at least a portion of the thrombus to the mesh; and removing the medical device from the blood vessel with at least the attached portion of the thrombus.

21. The method of Clause 20, wherein the galvanic cell is activated in the blood vessel.

22. The method of Clause 21, wherein the galvanic cell is activated while the mesh is engaged with the thrombus.

23. The method of Clause 20, wherein galvanically assisting attachment of at least a portion of the thrombus comprises binding, through a galvanic reaction, blood constituents to an anode of the galvanic cell.

24. The method of Clause 23, wherein the blood constituents are bound primarily to an inwardly facing surface of the mesh.

25. The method of Clause 24, wherein the blood constituents are bound substantially only to an inwardly facing surface of the mesh.

26. The method of Clause 20, wherein the blood vessel comprises an intracranial blood vessel.

27. The method of Clause 20, wherein inserting the medical device comprises inserting it to a location laterally adjacent to at least a portion of the thrombus.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. For example, although some drawings show the implementation of a galvanic effect in embodiments of an expandable member 102, the present disclosure encompasses the implementation of a galvanic effect in other endovascular devices, or in any thrombectomy device. In some instances, well-known structures and components are shown in block diagram form in order to avoid obscuring the concepts of the subject technology.

Figure 1:
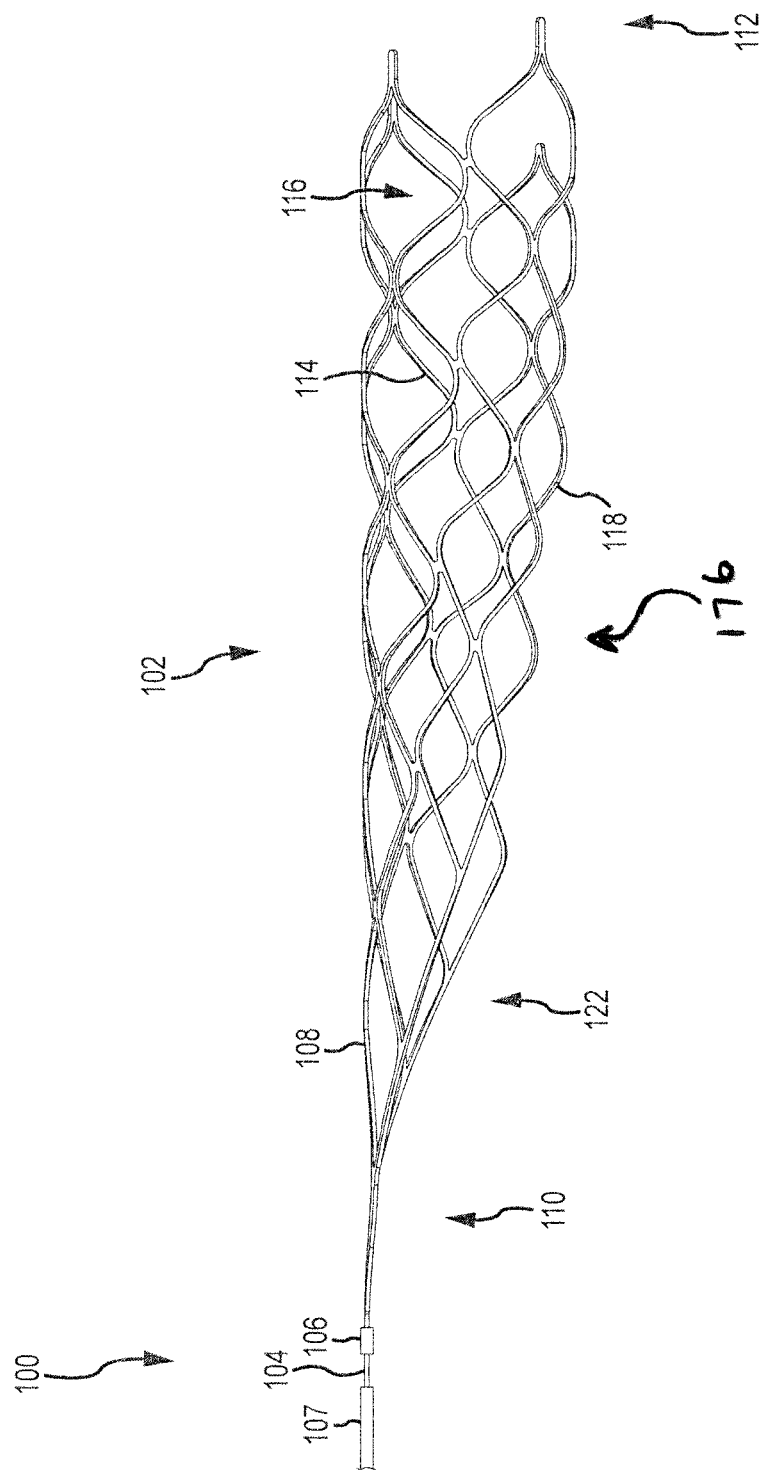
FIG. 1 illustrates a device, including an expandable member, for blood flow restoration, thrombus removal, or both, according to an embodiment.

FIG. 1 depicts a medical device 100 according to some embodiments of the subject technology. As illustrated in FIG. 1, the medical device 100 can comprise an engagement member such as the expandable member 102, and a manipulation member 104. A proximal end portion of the expandable member 102 and a distal end portion of the manipulation member 104 can be joined at a connection 106. The manipulation member 104 can extend through a catheter 107 such that an operator can manipulate the expandable member 102, positioned within and/or distal to a distal end of the catheter 107, using the manipulation member 104 at a location proximal to a proximal end of the catheter 107.

The manipulation member 104 can have a length sufficient to extend from a location outside the patient's body through the vasculature to a treatment site within the patient's body. The manipulation member 104 can be monolithic or formed of multiple joined components. In some embodiments, the manipulation member 104 can comprise a wire or a combination of wire(s), coil(s), and/or tube(s). The manipulation member 104 can comprise one or more markers, e.g., comprised of radiopaque material(s) to aid radiographic visualization during manipulation.

The expandable member 102 and the manipulation member 104 can be substantially permanently attached together at the connection 106. That is, the expandable member 102 and the manipulation member 104 can be attached together in a manner that, under the expected use conditions of the assembly 100, the endovascular device and the manipulation member would not become unintentionally separated from one another.

Depending on the procedure and intended use of the medical device 100, it optionally may be advantageous to have a connection mechanism that permits intentional release of the medical device 100. For example, during a blood flow restoration procedure, it may prove difficult and/or dangerous to fully retrieve a thrombus due to a complicated vasculature or the risk of damaging a lumen wall. Leaving the medical device 100 inside the patient may prove to be the only option available to a surgeon or other medical personnel, or it may be a goal of the procedure, such as when the device 100 is deployed across an aneurysm (e.g., as an aneurysm bridge to retain coils or other materials in an aneurysm). In other circumstances the medical device 100 may include drug-eluting capabilities, and/or may be coated with a particular type of drug that facilitates thrombus dissolution. It may be advantageous in such circumstances to release the medical device 100 and allow the medical device 100 to anchor the thrombus against the lumen wall while the thrombus is dissolved by the drug. In some embodiments, the medical device 100 can comprise a portion, located proximally or distally of the connection 106, that is configured for selective detachment of the endovascular device 102 from the manipulation member 104. For example, such a portion can comprise an electrolytically severable segment of the manipulation member. In some embodiments, the assembly 100 can be devoid of any feature that would permit selective detachment of the endovascular device 102 from the manipulation member 104.

Further details regarding connections that can be employed between the expandable member 102 and the manipulation member 104 disclosed in U.S. Patent Publication No. 2014/0194919, entitled Connection of an Endovascular Intervention Device to a Manipulation Member, published on Jul. 10, 2014; and U.S. Patent Publication No. 2014/0194911, entitled Connection of a Manipulation Member, Including a Bend without Substantial Surface Cracks, to an Endovascular Intervention Device, published on Jul. 20, 2014; and U.S. patent application Ser. No. 14/026,302, entitled Endovascular Device Engagement, filed on Sep. 13, 2013; the entirety of each of which is hereby incorporated by reference herein.

Figure 2:
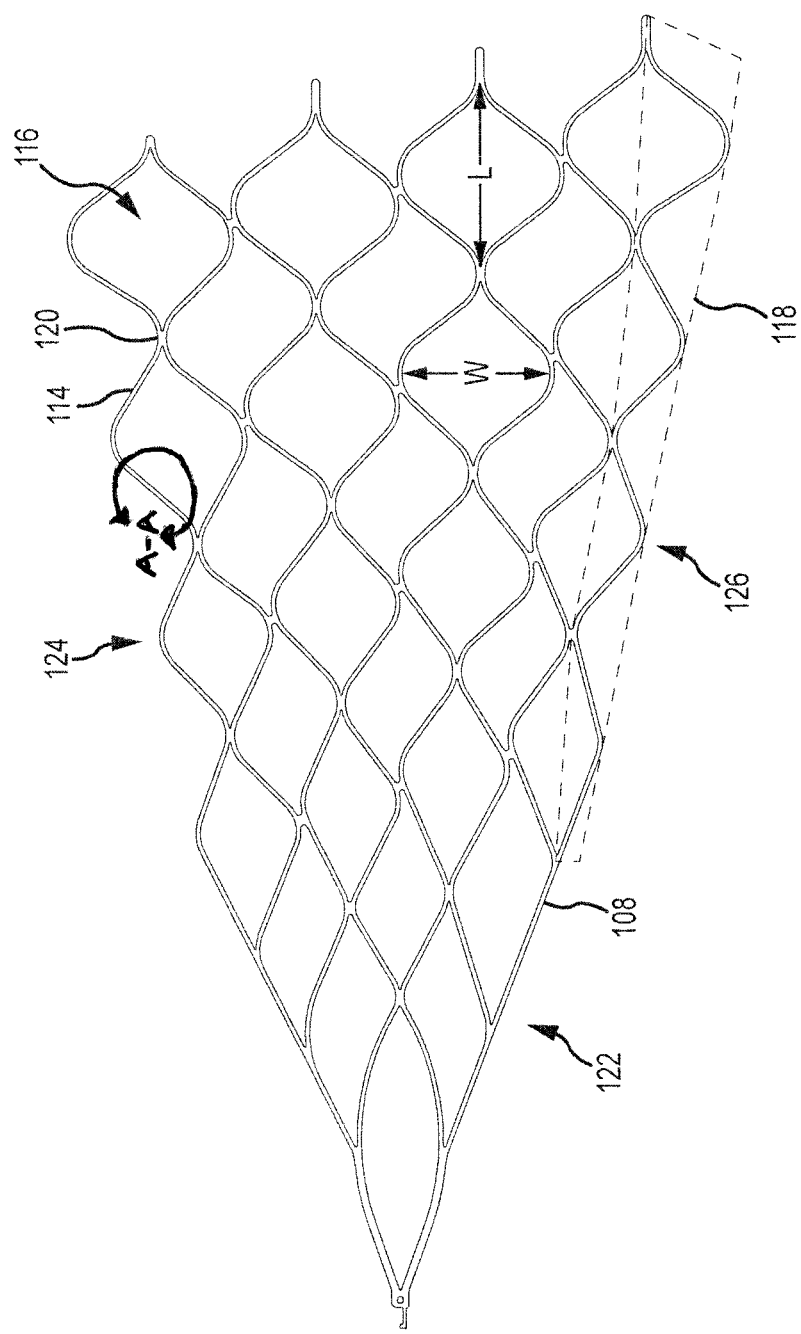
FIG. 2 illustrates an expandable member, according to an embodiment, in an unrolled state.
Figure 3:
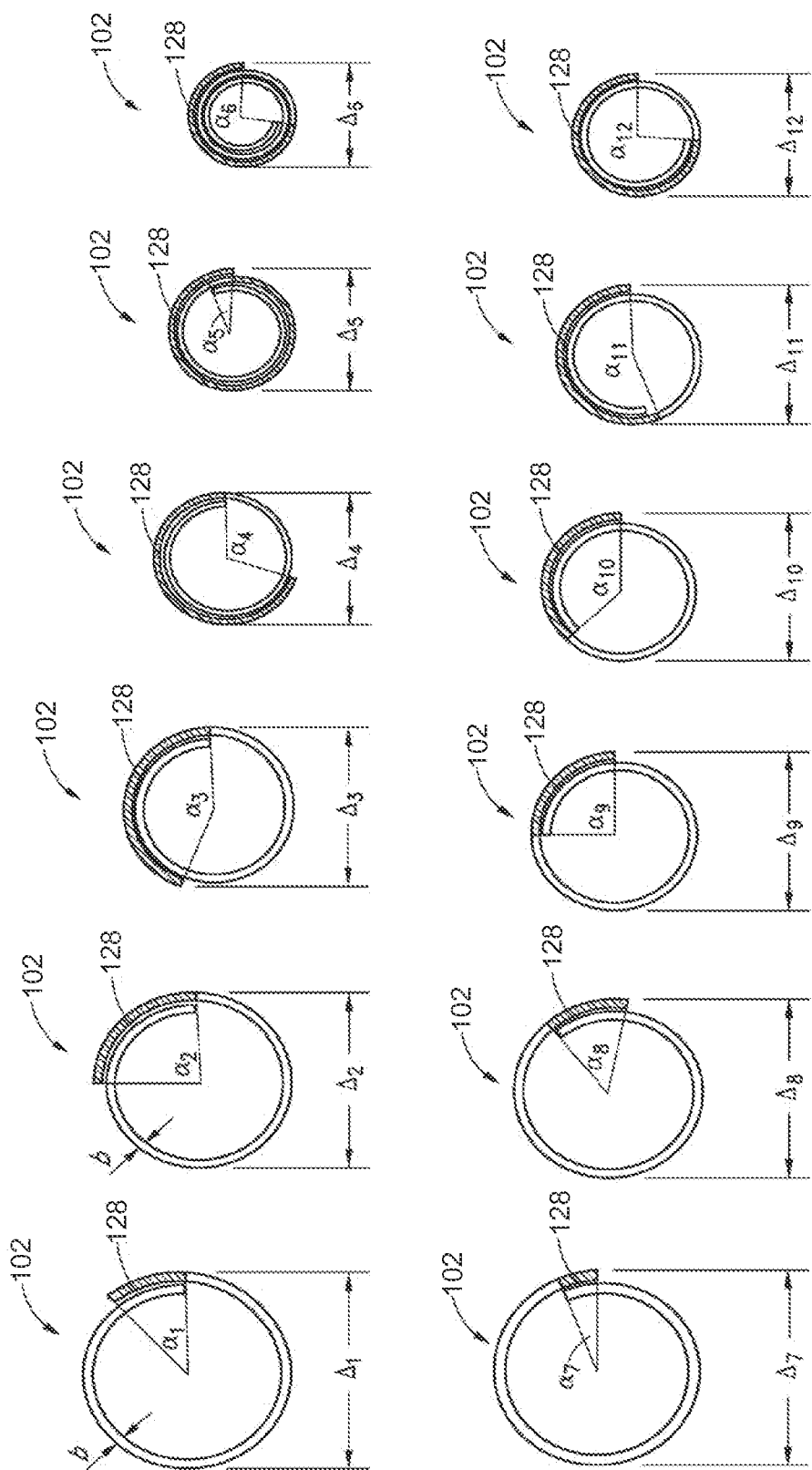
FIG. 3 is a schematic illustration of overlap configurations of the expandable member of FIG. 2, as viewed from a distal end of the expandable member.
Figure 4A:
FIGS. 4A-D are schematic illustrations of overlap configurations of the expandable member of FIG. 2, as viewed from a side of the expandable member.
Figure 4B:
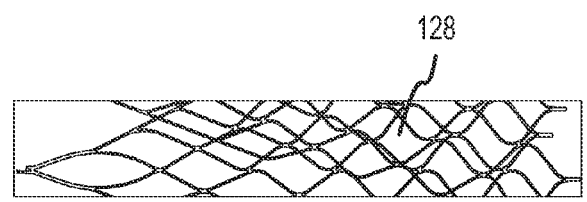
Figure 4C:
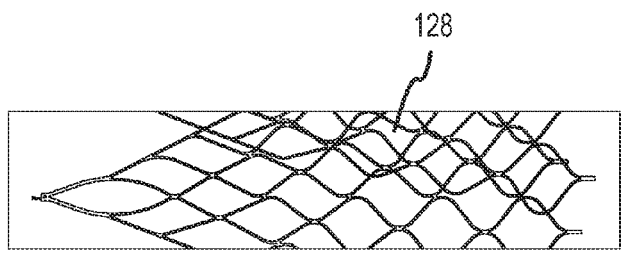
Figure 4D:
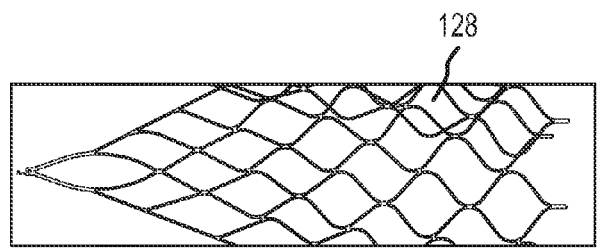

FIG. 2 is a plan view showing an embodiment of the expandable member 102 in an unrolled state to facilitate description and understanding. As illustrated in FIGS. 1 and 3, the expandable member 102 can have a tubular or generally cylindrical shape in absence of external forces in some embodiments. The expandable member 102 can be self-expanding, e.g. by super-elasticity or shape memory, or expandable in response to forces applied on the expandable member, e.g. by a balloon.

As illustrated in FIGS. 1 and 2, the expandable member 102 can comprise a frame 108 having a proximal end 110 and a distal end 112. The frame can optionally comprise a plurality of struts 114; the struts 114 can optionally be configured to define a plurality of cells 116 and/or form a mesh. Groups of longitudinally and serially interconnected struts 114 can form undulating members 118 that extend in a generally longitudinal direction. The struts 114 can be connected to each other by joints 120. While the struts are shown having a particular undulating or sinuous configurations, in some embodiments the struts can have other configurations. The frame can have a generally tubular or generally cylindrical shape with one or both of the proximal end 110 and the distal end 112 being open.

As illustrated in FIGS. 1 and 2, a proximal portion 122 of the expandable member 102 can be tapered toward the proximal end 110. In some embodiments, the taper of the proximal portion can advantageously facilitate retraction and repositioning of the device 100 and expandable member 102. In some embodiments, the tapered proximal portion can also be designed to generally not contact the vessel wall during a blood flow restoration procedure, and to generally not interfere with the flow of blood within a vessel.

Individual cells of the proximal portion 122 can have different sizes than individual cells located distal to the tapered proximal portion. For example, in some embodiments, the proximal portion 122 can have individual cells that have a size larger than that of the individual cells located distal to the tapered proximal portion. The proximal portion 122 can taper gradually towards the connection 106.

The taper of proximal portion 122 can be at various angles relative to the manipulation member 104. For example, in some embodiments, the taper can have an angle of approximately 45 degrees relative to the manipulation member, though other angles are also possible.

The expandable member 102 can comprise a first edge 124 and a second edge 126. The first edge 124 and second edge 126 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 124, 126 can be curved, straight, or a combination thereof along the tapered proximal portion 122.

The various embodiments of the expandable member 102 that are depicted or described herein provide one type of endovascular device or engagement member that may be employed as part of the medical device 100, for example coupled to a distal end or portion of the manipulation member 104, for functions such as removal or clots, thrombus or other obstructions from the body. The engagement member can be expandable (either self-expandable or not), or non-expandable. The engagement member can be generally tubular (as in the depicted expandable member 102) in its deployed state, or it can have other forms when deployed. The engagement member can optionally form a mesh (as in the depicted expandable member 102), or it can have other structural configurations. The engagement member, when deployed, can form a body that extends along a central longitudinal axis that can be generally aligned or coincident with a central longitudinal axis of the manipulation member 104, and/or with a central longitudinal axis of the vessel in which the engagement member is deployed. The engagement member body can form an outer surface having (a) an outward-facing portion that faces radially outward, away from any one or more of the central longitudinal axes specified above, (b) an inward-facing portion that faces radially inward, toward any one or more of the central longitudinal axes specified above, and/or (c) a laterally-facing portion that faces in a direction generally parallel to any one or more of the central longitudinal axes specified above. Therefore, the discussion provided elsewhere herein regarding the presence or disposition of metals that can provide a galvanic effect (e.g., a first metal and a second metal, or an anodic metal and a cathodic metal), and the various described embodiments, configurations and alternatives for implementing such concepts, apply to the engagement member as well, and accordingly such a galvanic effect can be provided in or on the engagement member.

Referring to FIGS. 3 and 4A-D, the expandable member 102 can be curled, rolled, or otherwise formed such that first edge 124 and second edge 126 overlap one another when the expandable member 102 is in a volume-reduced form. In a volume-reduced form, the frame 108 of the expandable member 102 can overlap to facilitate introduction of the expandable member 102 into and through the catheter 107. In some embodiments, the expandable member 102 is circumferentially continuous (e.g., forming a continuous cylindrical shape), lacking first and second edges 124, 126 and having no overlap or gap in a volume-reduced form and expanded form. Regardless of whether the expandable member is circumferentially continuous, the expandable member 102 can have a central longitudinal axis both while in a volume-reduce form and when fully or partially expanded. In some embodiments, the expandable member 102 can be self-expandable, and can expand toward a fully expanded configuration upon release from the catheter 107. Upon expansion, the expandable member 102 can expand towards an inner wall of a vessel, towards a thrombus occluding the inner wall of a vessel, or both.

FIGS. 4A-4D illustrate various amounts of overlap of the frame 108 of the expandable member 102. The extent of any overlap of the frame 108 can depend upon a degree of the frame's expansion. Expansion within a vessel can be limited, at least in part, by the vessel's size, and the amount and the properties of any thrombus present. For example, a greater overlap of the edges 124, 126 can occur in narrower vessels, whereas in wider vessels the overlap can be smaller, or even an "underlap" may occur, in which case the edges 124 and 126 are separated by an open gap or space within the vessel.

With continued reference to FIGS. 3 and 4A-D, embodiments of the expandable member 102 can experience various degrees of overlap in a volume-reduced form, forming zones of overlap 128. The expandable member 102 can assume various diameters $\Delta_1$, $\Delta_2$, etc., depending on the degree of the overlap (e.g. represented by angle $\alpha_1$, $\alpha_2$, etc.). As illustrated in FIGS. 4A-D, the overlap zones 128 can vary in size and configuration depending on the vessel size. When inside a vessel, the overlap zone of the expandable member 102 can advantageously provide grip and/or retaining ability with respect to a thrombus. For example, when the expandable member 102 expands against a thrombus, the individual struts 114 and individual cells 116 of the overlap zone can embed into and grip, or retain, the thrombus. Alternatively, the expandable member 102 can be constructed without any overlap or edges 124, 126, e.g. as a continuous tubelike or cylindrical member.

The expandable member 102 can be manufactured in various lengths and relaxed-state diameters. In some embodiments, the expandable member 102 can have lengths, measured proximally to distally along the longitudinal axis, of 15 mm or less to 40 mm or more, though other ranges and sizes are also possible. The expandable member 102 can also have relaxed-state diameters, the diameters being measured when the expandable member 102 is fully free to expand, i.e., in absence of external forces. In some embodiments, the expandable member 102 can have a diameter of approximately 3 mm to 4 mm so as to be used in size 18 microcatheters (i.e. microcatheters with an inner diameter of approximately 0.21 inch). In some embodiments the expandable member 102 can have a diameter of approximately 5 mm to 6 mm so as to be used in size 27 microcatheters (i.e. microcatheters with an inner diameter of approximately 0.027 inch). Other ranges and values are also possible.

Each cell 116 of the expandable member 102 can have a maximum length (labeled "L" in FIG. 2), as measured along a longitudinal axis of the expandable member 102, and a maximum width W, as measured along a direction generally perpendicular to the length (labeled "W" in FIG. 2). In some embodiments, cell size and dimensions can vary, as can the individual filament thicknesses and widths.

The location and longitudinal extent of thrombus engagement by a mechanical thrombus-retrieval device, e.g., the expandable member 102, can affect the likelihood of successfully capturing the engaged thrombus. Some embodiments of the subject technology increase the likelihood of successful thrombus capture and retrieval by increasing a longitudinal extent of substantially even thrombus engagement, distally shifting the region of increased thrombus engagement, or both. When a thrombus is primarily engaged along a portion of the thrombus near its proximal end, and particularly when a longitudinal extent of substantially even thrombus engagement is small, the thrombus may be more likely to fragment, become released from the retrieval device, or both.

In some embodiments, the expandable member 102 can be configured for substantially uniform or distally biased thrombus engagement, after expansion of the expandable member 102 into the thrombus, during retrieval of thrombus from a vessel by proximal retraction of the manipulation member 104. The thrombus can be generally soft, or malleable, or generally hard, or callous. For example, the expandable member 102 can have strut and cell dimensions that provide substantially uniform or distally biased thrombus engagement.

Figure 5:
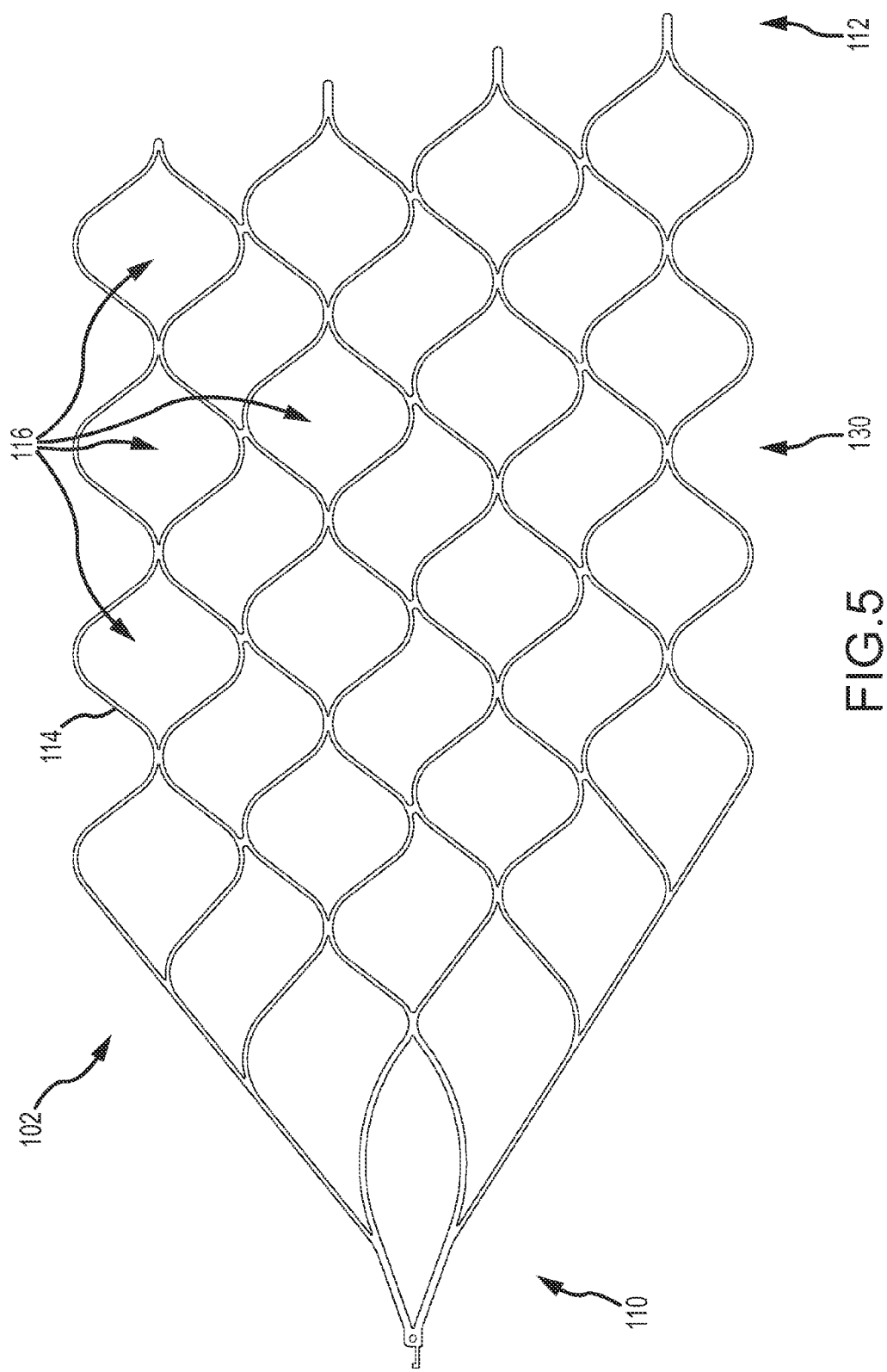
FIG. 5 illustrates an expandable member in an unrolled state.

FIG. 5 illustrates an expandable member 102 having a pattern 130 of cells 116 of substantially uniform dimensions and of struts 114 of substantially uniform dimensions. The pattern of cells and struts of FIG. 5 is substantially uniformly flexible or deformable. However, when the expandable member of FIG. 5 is embedded in a thrombus and a proximally directed force is applied at a proximal end 110 of the expandable member, the cells of the expandable member tend to collapse in width, and therefore engage a thrombus, more along a proximal portion of the substantially uniform pattern 130 than they do along a distal portion of the substantially uniform pattern 130. Such a proximally directed force may be considered to simulate the force exerted on the proximal end 110, via the manipulation member 104, during retrieval of the expandable member 102 in a procedure to remove, e.g., thrombus from a blood vessel.

Figure 6B:
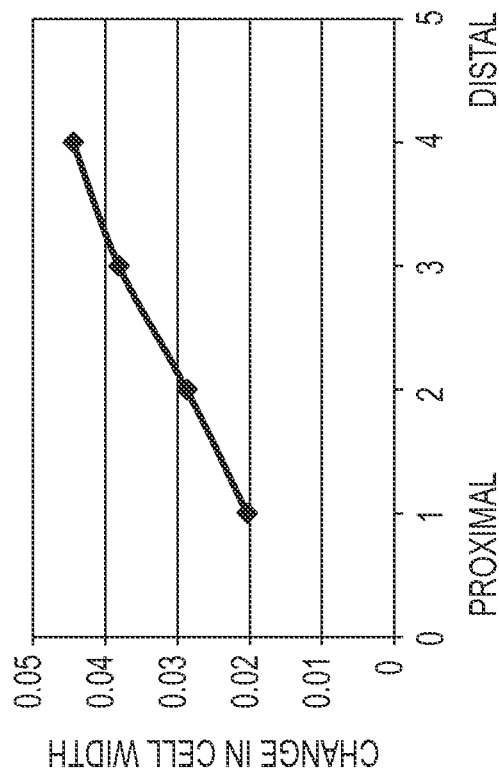
FIGS. 6A and 6B illustrate change in lateral cell width for various locations along expandable members.
Figure 6A:
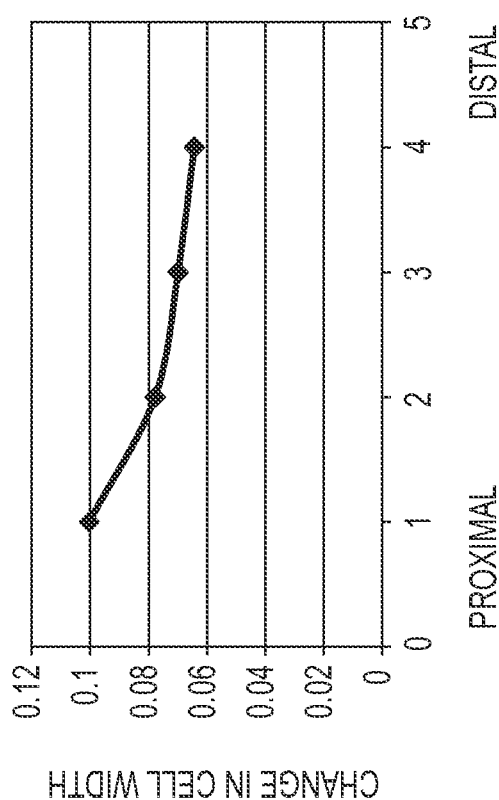

FIGS. 6A and 6B illustrate the amount of change (reduction) in (e.g., maximum) cell width W observed for cells in various longitudinal positions along the length of the frame 108, upon application of a proximally directed force at a proximal end of the frame when embedded in simulated thrombus having an outer extent fixed in six degrees of freedom. FIG. 6A is an exemplifying plot of the amount of change (reduction) in (maximum) cell width (resulting from such force application) against longitudinal position for a frame having a substantially uniform cell angle or pattern 130. As indicated by FIG. 6A, the amount of change in maximum cell width diminishes with distance from the proximal end for a frame having a substantially uniform pattern 130. Thus, an expandable member having a substantially uniform pattern 130 "pinches" the thrombus more (by virtue of a greater reduction in cell width) along a proximal portion of the thrombus than it does along a distal portion of the thrombus.

FIG. 6B is an exemplifying plot of the amount of change (reduction) in (maximum) cell width against the longitudinal position for frames in some embodiments of the subject technology, for example such as those illustrated in FIGS. 2, 8, 9, and 10. In contrast to FIG. 6A, FIG. 6B indicates that the amount of reduction in maximum cell width increases with distance from the proximal end for frames according to some embodiments of the subject technology. Thus, an expandable member according to some embodiments of the subject technology pinches and grips the thrombus more along a distal portion of the thrombus than it does along a proximal portion of the thrombus. Therefore, expandable members according to some embodiments of the subject technology can be less likely to fragment the thrombus, release the thrombus, or both during retrieval, compared to an expandable member having a substantially uniform pattern 130.

Figure 7A:
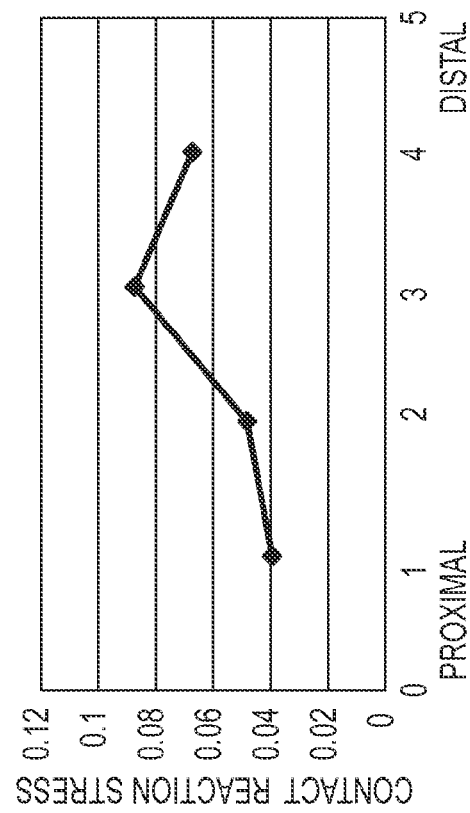
FIGS. 7A and 7B illustrate associated contact reaction stress of the clot for various locations along expandable members, as a consequence of the change in lateral cell width illustrated in FIGS. 6A-6B.
Figure 7B:
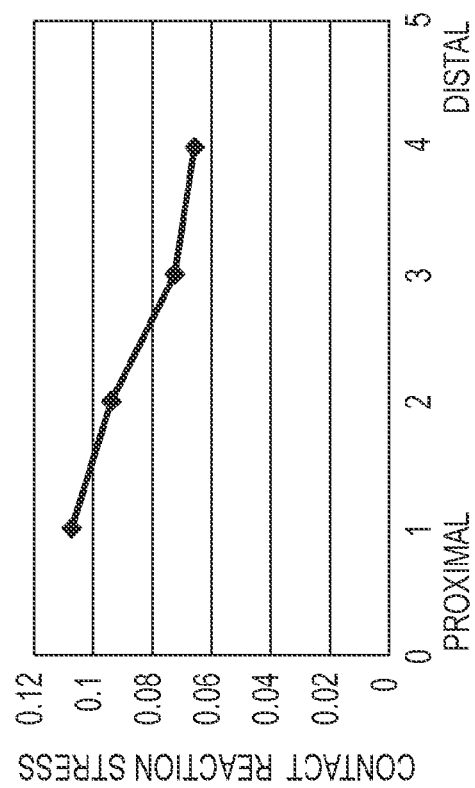

FIGS. 7A and 7B indicate the resultant contact reaction stresses (due to the cell width reduction) between the frame and thrombus in cells at various longitudinal positions along the length of the frame, upon application of a proximally directed force at a proximal end of the frame when embedded in simulated thrombus having an outer extent fixed in six degrees of freedom. FIG. 7A is an exemplifying plot of contact reaction stress against longitudinal position for a frame, as illustrated in FIG. 5 for example, wherein longitudinally and laterally adjacent cells have substantially the same dimensions and the struts surrounding those cells have substantially the same dimensions. As indicated by FIG. 7A, contact reaction stress diminishes with distance from the proximal end for a frame having a substantially uniform pattern 130. Thus, an expandable member having a substantially uniform pattern 130 tends to pull on the thrombus, during retraction, more along a proximal portion of the thrombus than it does along a distal portion of the thrombus.

FIG. 7B is an exemplifying plot of contact reaction stress against longitudinal position for frames in some embodiments of the subject technology, for example such as those illustrated in FIGS. 2, 8, 9, and 10. In contrast to FIG. 7A, FIG. 7B indicates that contact reaction stress increases, along at least a portion of the frame's length, with distance from the proximal end for frames according to some embodiments of the subject technology. Thus, an expandable member according to some embodiments of the subject technology tends to pull on the thrombus less along a proximal portion of the thrombus than it does along a portion of the thrombus distal to the proximal portion. Therefore, expandable members according to some embodiments of the subject technology can be less likely to fragment the thrombus, release the thrombus, or both during retraction, compared to an expandable member having a substantially uniform pattern 130.

Figure 8:
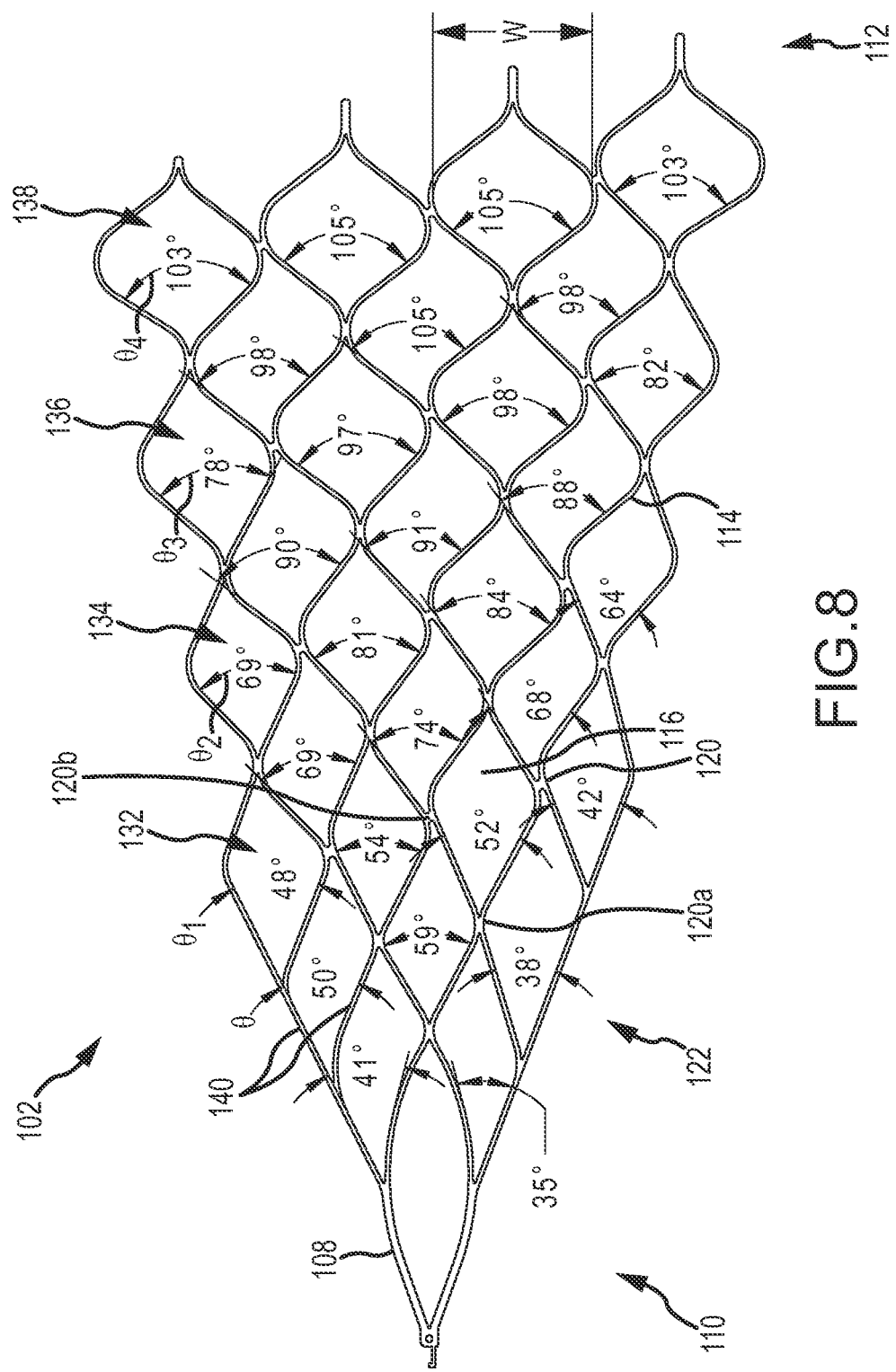
FIG. 8 illustrates an expandable member, according to an embodiment, in an unrolled state.
Figure 9:
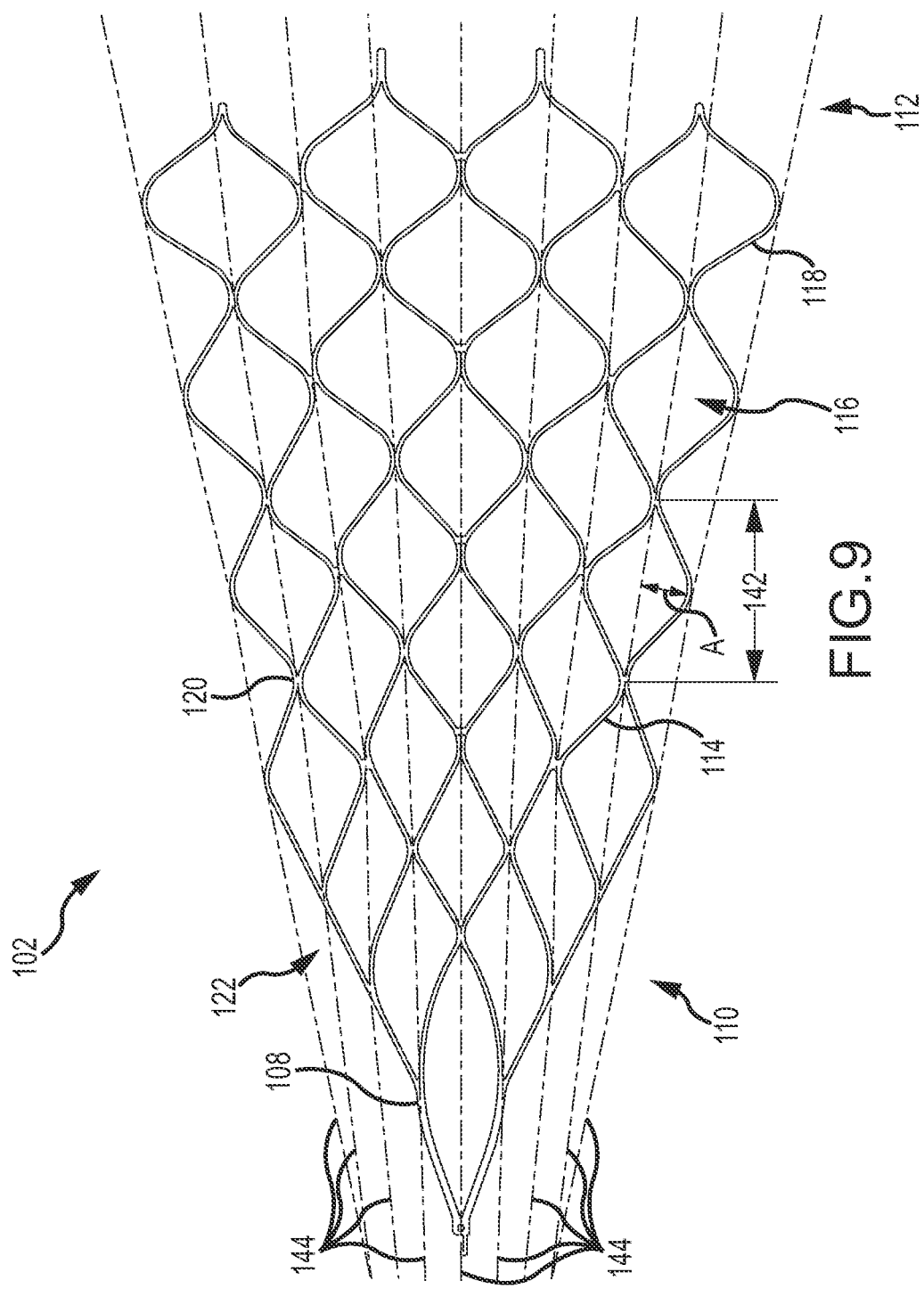
FIG. 9 illustrates an expandable member, according to an embodiment, in an unrolled state.
Figure 10:
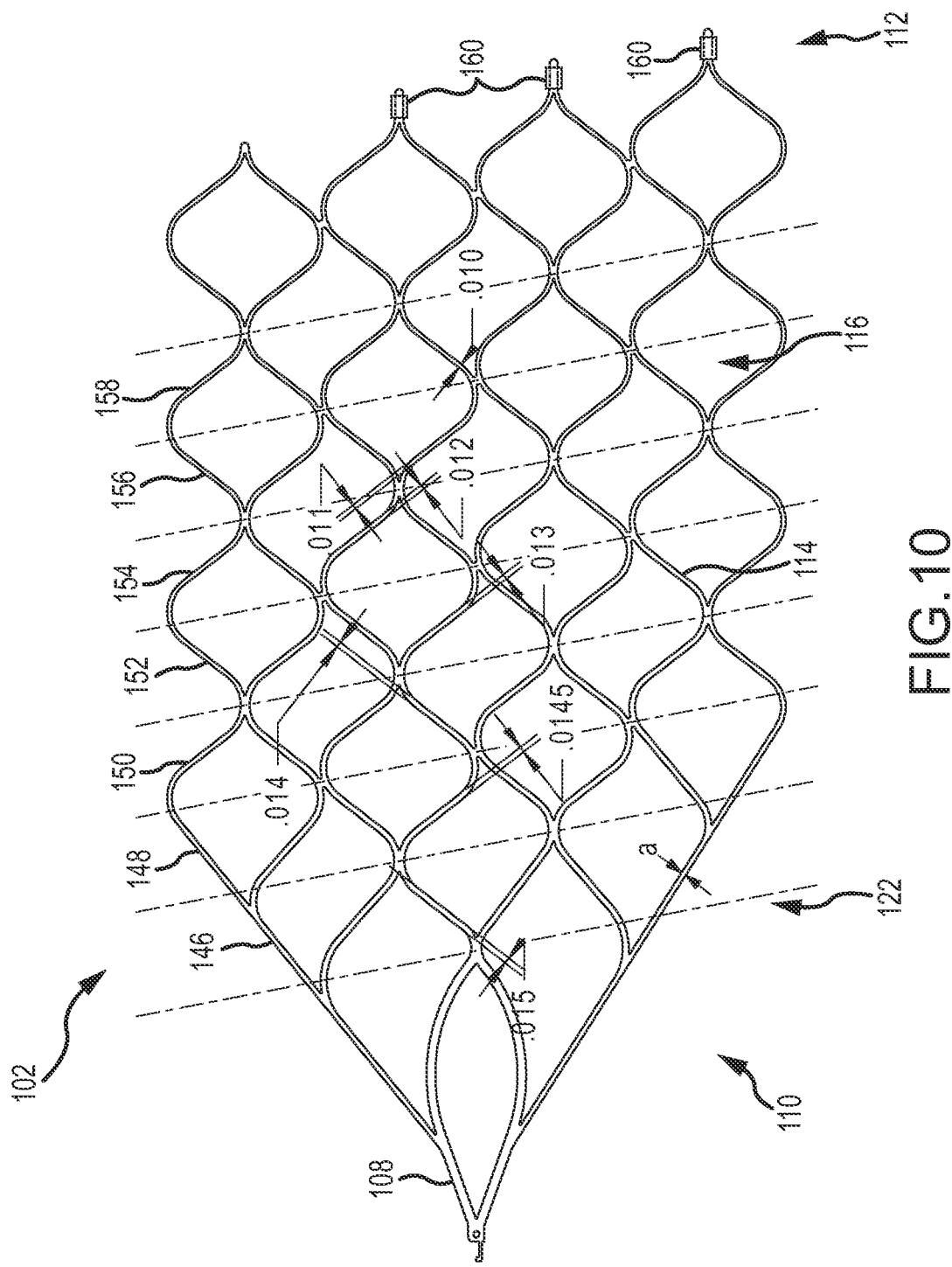
FIG. 10 illustrates an expandable member, according to an embodiment, in an unrolled state.

FIGS. 8-10 illustrate expandable members 102, according to embodiments of the subject technology, in plan view, e.g., an unrolled state. The expandable members 102 of FIGS. 8-10 are examples of the expandable member 102 described above with reference to FIGS. 2-4D. Accordingly, the description of the expandable member 102 with reference to FIGS. 2-4D also applies to expandable members 102 of FIGS. 8-10.

The expandable members 102 of FIGS. 8-10 can provide distally biased thrombus engagement, as described above with reference to FIGS. 6B and/or 7B, substantially uniform thrombus engagement, or a combination thereof over lengthwise portions of the expandable member. Thrombus engagement can be considered substantially uniform when the amount of change in maximum cell width and/or contact reaction stress varies in the longitudinal direction by less than 5% upon application of a proximally directed force at a proximal end of the expandable member when the expandable member is embedded in thrombus, or simulated thrombus, having an outer extent fixed in six degrees of freedom.

In some embodiments, at least a portion of the frame 108, from a first location to a second location along the frame, is configured such that an amount of cell deformation or deflection in response to longitudinally directed tensile forces decreases by less than 5% or increases in a distal direction along a portion of the frame. The cell deformation can be, for example, change of maximum cell width. In some embodiments, the amount of cell deformation in response to longitudinally directed tensile forces does not decrease in a distal direction along the portion of the frame. In some embodiments, the amount of cell deformation in response to longitudinally directed tensile forces continuously increases in a distal direction along the portion of the frame. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, at least a portion of the frame 108, from a first location to a second location along the frame, is configured such that an amount of thrombus engagement in response to longitudinally directed tensile forces decreases by less than 5% or increases in a distal direction along a portion of the frame. The thrombus engagement can be, for example, contact reaction stress. In some embodiments, the amount of thrombus engagement in response to longitudinally directed tensile forces does not decrease in a distal direction along the portion of the frame. In some embodiments, the amount of thrombus engagement in response to longitudinally directed tensile forces continuously increases in a distal direction along the portion of the frame. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

FIG. 8 illustrates an expandable member 102 wherein, in a portion of the frame 108 in a relaxed state, each cell distally adjacent to another cell, in a longitudinal row of cells, has a larger proximal inscribed strut angle θ between first and second struts (i) bounding a proximal portion of the cell and (ii) diverging in a distal direction, than has the another cell. For example, FIG. 8 shows a first cell 132 having a proximal inscribed strut angle $\theta_1$, a second cell 134 having a proximal inscribed strut angle $\theta_2$, a third cell 136 having a proximal inscribed strut angle $\theta_3$, and a fourth cell having a proximal inscribed strut angle $\theta_4$, wherein $\theta_4 > \theta_3 > \theta_2 > \theta_1$. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, the proximal inscribed strut angle $\theta$ can be measured between substantially straight portions 140 of the struts 114, as illustrated in FIG. 8. In some embodiments, the proximal inscribed strut angle $\theta$ can be measured between straight reference lines that connect a joint 120a, at a proximal end of a cell, with opposing laterally positioned joints 120b, 120c, respectively, at of that cell. In either case, each strut 114 can be straight, curved, or comprise straight portion(s) and curved portion(s).

In addition or alternative to distally increasing, proximal inscribed strut angles, the expandable member 102 can have a portion of the frame 108 wherein, in a relaxed state, each cell distally adjacent to another cell, in a longitudinal row of cells, has a larger interior bounded area than has the another cell. For example, an interior bounded area of fourth cell 138 can be larger than an interior bounded area of third cell 136, which can be larger than an interior bounded area of second cell 134, which can be larger than an interior bounded area of first cell 132. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

In some embodiments, the expandable member 102 can have a portion of the frame 108 wherein, in a relaxed state, each cell distally adjacent to another cell, in a longitudinal row of cells, has a larger maximum cell width W than has the another cell. For example, a maximum cell width of fourth cell 138 can be larger than a maximum cell width of third cell 136, which can be larger than a maximum cell width of second cell 134, which can be larger than a maximum cell width of first cell 132. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

Accordingly, the herein-discussed configurations of the expandable member 102 (distally increasing maximum cell width W, distally increasing cell area, distally increasing proximal included strut angle $\theta$, distally increasing amplitude A, distally diverging reference lines 144, and/or distally increasing strut flexibility/deflectability) can each be considered a means for engaging a thrombus (or other material) in a substantially uniform (and/or distally biased) manner along the length of the expandable member 102.

In the embodiment of FIG. 8, maximum cell length can range from 3.50 mm to 5.50 mm in a relaxed state, though other ranges and values are also possible, and maximum cell width can range from between 2.50 mm to 4.50 mm and a relaxed state, though other ranges and values are also possible. All of the foregoing dimensions can optionally be implemented alone or in any combination without departing from the scope of this disclosure.

FIG. 9 illustrates an expandable member 102 comprising a plurality of undulating or sinuous members 118. Each undulating or sinuous member 118 can comprise a plurality of oscillations 142. Each oscillation can have an amplitude (labeled "A" in FIG. 9). In some embodiments, an oscillation can correspond in length to the length of a cell. An oscillation 142 can comprise one or more struts 114. Some embodiments can comprise a portion of the frame 108 wherein, in a relaxed state, each oscillation of each undulating or sinuous member 118 does not decrease, or alternatively, increases in a distal direction compared to a proximally adjacent oscillation. In some embodiments, the amplitude of the oscillations can increase distally at a constant rate per unit length. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

FIG. 9 illustrates a plurality of reference lines 144. Each reference line can pass through all joints 120 between adjacent cells in a row of cells. Some embodiments can comprise a portion of the frame 108 wherein, in a relaxed state, each reference line 144 continuously diverges from at least one or two adjacent reference lines 144. In some embodiments, the reference lines can be straight. In some embodiments, all or a portion of respective reference line can be curved. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, the portion of the frame can comprise a longitudinal row of at least two, three, or four cells.

In some embodiments, the expandable member 102 can have a portion of the frame 108 wherein, in a relaxed state, each cell distally adjacent to another cell can have a strut that is more flexible or deflectable than a strut of the another cell. In some embodiments, each strut distally adjacent to another strut can be more flexible or deflectable than is the another strut. Strut flexibility or delectability can be increased, for example, by diminishing strut thickness, strut width, or both along all or a portion of the strut's length. The portion of the frame can extend from a first location to a second location along the frame. In some embodiments, the first and second locations can be longitudinally separated by a distance that is more than half of the mesh length, at least two thirds of the frame length, at least three quarters of the frame length, or at least 90% of the frame length. In some embodiments, portion of the frame can comprise a longitudinal row of at least two, three, or four cells.

The struts 114 can have individual strut widths "a" (FIG. 10) that range from 0.010 in. to 0.025 in., and individual strut thicknesses "b" that range from 0.045 mm to 0.080 mm, though other ranges and values for individual strut width and thickness are also possible. Widths "a" as described herein can generally be measured as illustrated by the arrows in FIG. 10. Thicknesses "b" as described herein can generally be measured as illustrated by the arrows in FIG. 3 (e.g. in a direction extending out of the page of FIG. 10, and perpendicular to the measurement for width "a"). The widths "a" can be measured, for example, using a system such as the Visicon Automated Inspection System, or other suitable system. The thicknesses "b" can be measured, for example, using a system such as the Heidenhain Inspection System, or other suitable system.

With continued reference to FIG. 10, the joints 120 can have an individual strut thickness "b" that range from 0.050 mm to 0.0825 mm and an individual strut width "a" that ranges from 0.050 mm to 0.0825 mm, though other ranges and values are also possible. In some embodiments, individual struts can have individual strut thicknesses "b" that range from 0.040 mm to 0.075 mm, and individual strut widths "a" that range from 0.038 mm to 0.082 mm, though other ranges and values are also possible. In some embodiments, the individual struts in a portion of the expandable member 102 can have average strut thicknesses "b" that range from 0.048 mm to 0.067 mm, and individual strut widths "a" that average from 0.053 mm to 0.067 mm, though other ranges for average values are also possible.

FIG. 10 illustrates an example of an embodiment wherein strut thickness is diminished in a distal direction, thereby distally increasing strut flexibility or to flexibility. The frame 108 of the expandable member 102 in FIG. 10 comprises a plurality of rings 146, 148, 150, 152, 154, 156, 158 of circumferentially adjacent struts. The struts 114 in each ring can have substantially the same width, as illustrated, for example, in FIG. 10. In some embodiments, circumferentially adjacent struts can have different widths. Referring again to FIG. 10, the strut width of each ring 146, 148, 150, 152, 154, 156, 158 can diminish in the distal direction. In other words, a strut width of ring 158 can be less than a strut width of ring 156, which can be less than a strut width of ring of 154, which can be less than a strut width of ring 152, which can be less than a strut width of ring 150, which can be less than a strut width of ring 148, which can be less than a strut width of ring 146. In some embodiments, two or more longitudinally adjacent struts, or rings of struts, can have the same, or substantially the same, width. For example, struts 114 distal to the ring 158 can have the same, or substantially the same, strut width as the struts of ring 158.

Although FIG. 10 illustrates the struts 114 as having substantially constant widths along their entire respective lengths, the struts can have widths that vary along their lengths in some embodiments. For example, the struts can have an hourglass shape, can be wider in the middle than at the ends, can have corrugated edges, or have other configurations. Strut thickness can likewise be constant or variable along each strut's length. The struts' cross-sectional areas can likewise be constant or variable along each strut's length.

In the embodiment of FIG. 10, maximum cell length can range from 3.50 mm to 5.50 mm in a relaxed state, though other ranges and values are also possible and within the scope of this disclosure, and maximum cell width can range from between 2.50 mm to 4.50 mm and a relaxed state, though other ranges and values are also possible and within the scope of this disclosure.

The expandable member 102 can generate specific forces once it is deployed and released from the catheter 107 for engagement and removal of thrombi. By deploying the expandable member 102 in or across a thrombus, the expandable member 102 can be expanded, e.g., self-expanded to a larger diameter due to elastic energy stored in the expandable member 102. The expandable member 102 can expand in the vessel until equilibrium is reached between the stored elastic energy and an opposing force from the surrounding vessel wall and/or thrombus. The struts 114 and cells 116 of the expandable member 102 can penetrate a thrombus, promoting adhesion and embedment of the thrombus to the expandable member 102, and the expanding force of the expandable member 102 can promote dislodgment of the thrombus from the vessel wall.

In some embodiments, the expandable member 102 can further include at least one distal marker 160. The distal marker 160 can be attached to or integrally formed with a distal portion of the expandable member 102. The distal marks 160 can comprise, for example, a band comprising platinum, gold, and/or other radiopaque materials. The markers 160 can be used during an imaging process to identify a location or locations of the expandable member 102 during a blood flow restoration procedure. PCT Publication No. WO 2009/105710, which is incorporated by reference in its entirety, describes various uses of marker bands and imaging of an expandable member 102.

The frame 108 can be formed, for example, by cutting a sheet or tube (e.g., by laser, etching, etc.), by interconnecting a multitude of filaments by laser welding, or by other suitable methods. In some embodiments, the expandable member 102 can be initially laser cut from a tube. In some embodiments, the expandable member 102 can be formed by cutting a pattern on a flat sheet and then rolling the flat sheet into a generally tube-like or coiled shape. The joints 120 may be formed by welding, soldering, or otherwise joining the struts 114. Other methods for forming the expandable member 102 are also possible.

In some embodiments, the endovascular device, engagement member or expandable member 102 can comprise metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. In some embodiments, the expandable member may be formed from materials having shape memory properties. Where a galvanic effect is desired, the endovascular device, engagement member or expandable member 102 should be formed from metal, or from a non-metal that is coated with metal.

In some embodiments, the endovascular device, engagement member or expandable member 102 can have a galvanic cell or a plurality of galvanic cells formed on a surface thereof. Such galvanic cell(s) can generate, in the presence of blood, thrombus, or other electrolytic medium, a voltage and/or electrical charge that enhances the capability of the expandable member 102 to grip thrombus. For example, the galvanic cell(s) can generate an electrical charge, or electrically charged region(s), on the endovascular device, engagement member or expandable member 102 that can attract, adhere, and/or attach thrombus to the expandable member 102 when the expandable member 102 is deployed next to or into thrombus in a blood vessel. The generated charge or charged regions on the expandable member 102 can have a charge opposite that of constituents of the thrombus. The generated charge or charged regions can include both regions of negative charge and regions of positive charge, each of which can attract, adhere, and/or attach to blood constituents or thrombus constituents of the opposite charge. The attraction, adhesion, and/or attachment of blood constituents to thrombus constituents may be electrostatic.

The galvanic cell(s) can comprise at least two different metals (as used herein, "metal" can refer to a pure or elemental metal, or to alloys), such as a first metal 180 and a second metal 182, that generate an electrical charge in the presence of an electrolytic medium, for example, such as blood. The metals may be characterized as having different reduction potentials or electrode potentials; various metal combinations may be determined with reference to the electromotive force (EMF) chart. The metals of the galvanic cell are in electrical contact, e.g., direct physical contact, with each other. The first metal 180 and second metal 182 can be selected to induce a galvanic voltage and impart a desired charge arrangement in a galvanic region. For example, the metals 180, 182 can be selected so that the first metal 180 functions as a cathode (having a positive charge) and the second metal 182 functions as an anode (having a negative charge), or vice versa. Any combination of anode and cathode metals can be employed. One useful combination is a first metal of nickel-titanium alloy, e.g., nitinol, and a second metal e.g. of magnesium, in which case the first metal can act as a cathode and as the structural metal of the endovascular device, engagement member or expandable member 102, and the second metal can act as an anode. The reverse can be employed as well, in which the first metal is magnesium and the second metal is nitinol.

In a single cell the nitinol-magnesium combination can induce a galvanic voltage of about 1.3 volts in saline. Other strongly anodic metals can be used as a first or second metal in combination with nitinol, for example lithium or zinc. Metals other than nitinol also can be used as a cathode, such as, for example, platinum, nickel, titanium, gold, graphite, and silver. The structural metal of the endovascular device, engagement member or expandable member 102 can also be employed as anode, where a metal that is cathodic relative to the structural metal is employed as the second metal. In a single expandable member 102 multiple types of first metals and/or multiple types of second metals can be employed. For example, one second metal type can be employed in one portion of the expandable member 102 and another second metal type can be employed in another portion of the expandable member 102. Metal combinations other than nitinol-magnesium may induce galvanic voltages different than does nitinol-magnesium. For example, a galvanic cell comprising nitinol and platinum can induce a galvanic voltage of about 0.49 volts in saline, and a galvanic cell comprising magnesium and platinum can induce a galvanic voltage of about 1.7 volts in saline.

FIGS. 11-14 illustrate several embodiments of the expandable member 102 or a portion of filament(s) 178 thereof, for example as in the area A-A in FIG. 2, that include one or more galvanic cells. Such cells can be formed by providing a first metal 180 and a second metal 182 disposed over and in electrical contact, e.g., direct physical contact, with the first metal. The first metal 180 can comprise, for example, the metal from which the frame 108 is or filaments 178 are fabricated. For example, when the expandable member 102 is laser cut from a nitinol tube, the first metal 180 can comprise nitinol. For convenience herein, such a metal can be considered the "structural metal" of the frame 108, filaments 178 and/or expandable member 102. The first metal 180 can alternatively comprise a metal which is plated, coated, deposited, or otherwise applied over some or all of the structural metal (or structural polymer) of the expandable member 102.

The second metal 182 can be coated, deposited, welded, plated, or otherwise applied over some or all of the structural metal (or structural polymer where a metal-coated polymer is employed) of the expandable member 102, which may be the first metal 180 or another metal. If the first metal 180 comprises a metal which is plated, coated, deposited, or otherwise applied over some or all of the structural metal (or structural polymer) of the expandable member 102, the second metal 182 can comprise the structural metal of the expandable member 102 or can be plated, coated, deposited, or otherwise applied over some or all of the structural metal (or structural polymer), which is neither the first metal nor the second metal.

Figure 17:
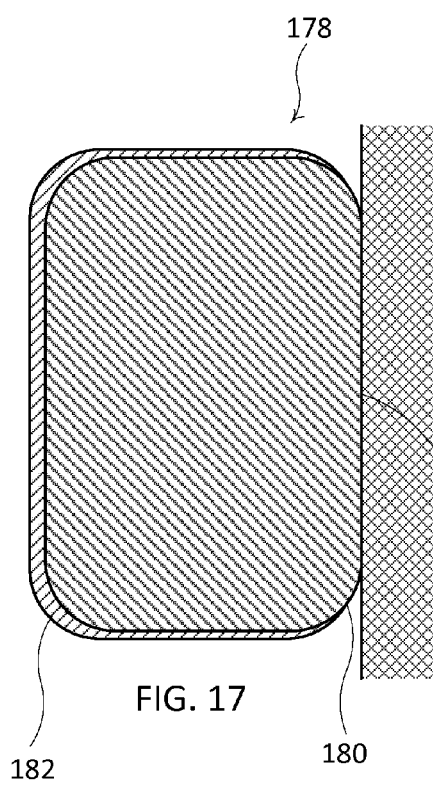

As seen in FIGS. 11-14, the second metal 182 can be arranged in an intermittent pattern of one or more discrete second metal regions on a region of the first metal 180 (or alternatively in a continuous layer over at least a portion of the first metal 180). One or more portions of the structural metal (or structural polymer) can be masked or otherwise covered (e.g., by a mandrel 186), for example as illustrated in FIG. 17, during plating, coating, deposition, or other application of the first metal, the second metal, or both on the structural metal (or structural polymer). The region of the first metal 180 can be continuous or generally continuous, including any portions thereof that underlie the second metal 182 regions. Accordingly, a galvanic region of the expandable member 102 can comprise a pattern of one or multiple discrete second metal 182 regions situated on or in a first metal 180 region, which first metal region can be continuous or generally continuous in the area(s) in which the galvanic region prevails. The galvanic region can prevail, for example, over the entire outer surface of the endovascular device, engagement member or expandable member 102, or over a selected portion thereof, such as the mesh (where present), a distal portion 176 and/or the proximal portion 122 (see FIG. 1). The galvanic region can prevail, for example, over any one or combination of the following: (a) some or all of the portion of the outer surface of the endovascular device, engagement member or expandable member 102 that faces radially outward, away from the central longitudinal axis of the endovascular device, engagement member or expandable member 102, (b) some or all of the portion of the outer surface of the endovascular device, engagement member or expandable member 102 that faces radially inward, toward the central longitudinal axis of the endovascular device, engagement member or expandable member 102, and (c) some or all of the portion of the outer surface of the endovascular device, engagement member or expandable member 102 that faces laterally toward the interior of a cell 116, or otherwise. Instead of or in addition to the foregoing, the galvanic region can be configured such that one, some or all cell(s) 116, and/or filament(s) 178, can have more than 1, 2, 3, 5, or 10 galvanic cells positioned on it.

Figure 12:
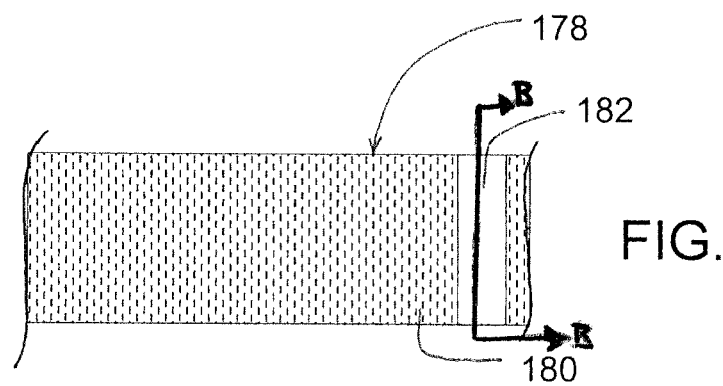
Figure 15:
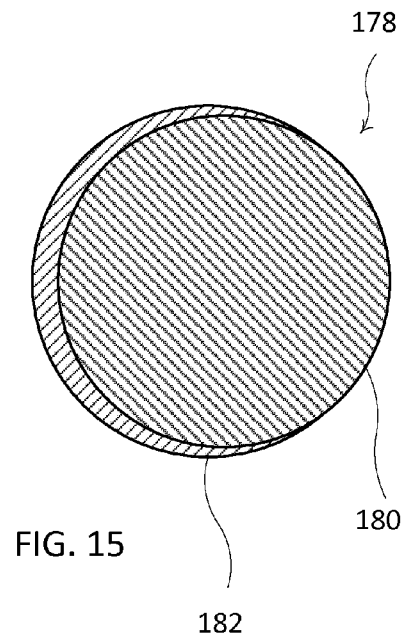
FIGS. 15-20 are schematic cross-sections of filaments, according to various embodiments.
Figure 16:
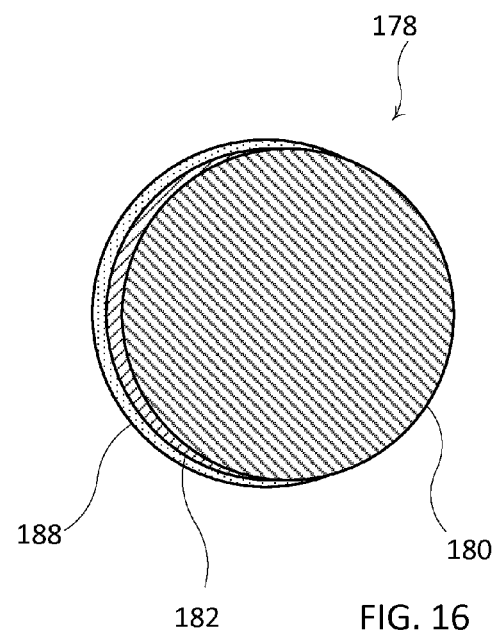
Figure 18:
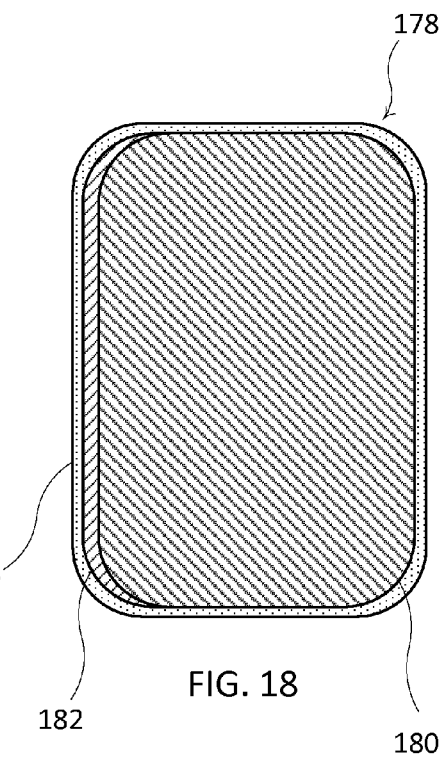

The locations (a), (b), and (c) are illustrated with respect to a single filament in FIGS. 15-18, which are schematic cross-sections of filaments 178, for example as taken along line B-B in FIG. 12. Each of the right and left directions in FIGS. 15-18 can be considered alternatively radially inward or outward. Accordingly, FIGS. 15-18 illustrate filaments having the first metal 180 prevailing over location (a) or (b)

and the second metal 182 prevailing over the other of location (a) or (b). In FIGS. 15 and 17, the second metal 182 also extends onto the location (a) or (b) on which the first metal 180 prevails, but the extension of the second metal on to such location is to a much smaller degree such that such location is substantially free of the second metal. In FIGS. 16 and 18, the second metal 182 does not extend onto the location (a) or (b) on which the first metal 180 prevails, such that such location is free of the second metal. FIGS. 15-18 also illustrate the filaments 178 having the first metal 180 and the second metal 182 over location (c), although in different proportions. Thus, location (c) may overlap somewhat with locations (a) and/or (b) depending on the shape of the filament.

In a single endovascular device, engagement member or expandable member 102 employing multiple types of first metals and/or multiple types of second metals, (i) one first metal type can be employed in one portion of the expandable member 102 (e.g., one of the locations (a), (b), (c) specified above) and another first metal type can be employed in another portion of the expandable member 102 (e.g., another of the locations (a), (b), (c)), and/or (ii) one second metal type can be employed in one portion of the expandable member 102 (e.g., one of the locations (a), (b), (c) specified above) and another second metal type can be employed in another portion of the expandable member 102 (e.g., another of the locations (a), (b), (c)).

Figure 11:
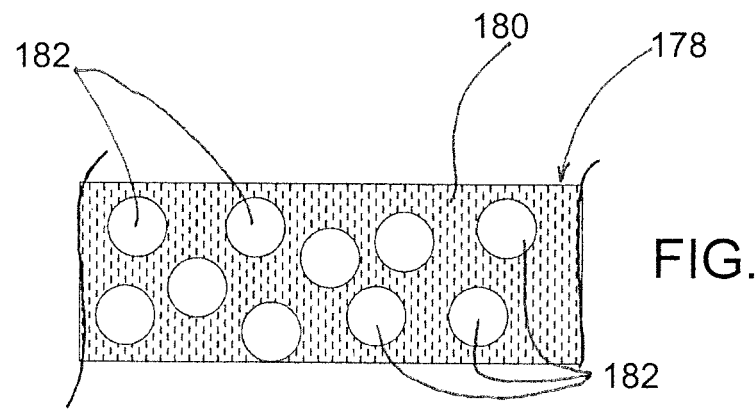
FIGS. 11-14 are schematic plan views of various embodiments of galvanic regions for use with the endovascular device of FIG. 2.
Figure 13:
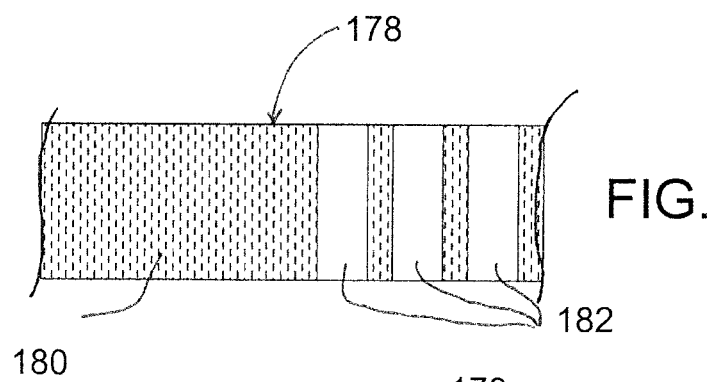
Figure 14:
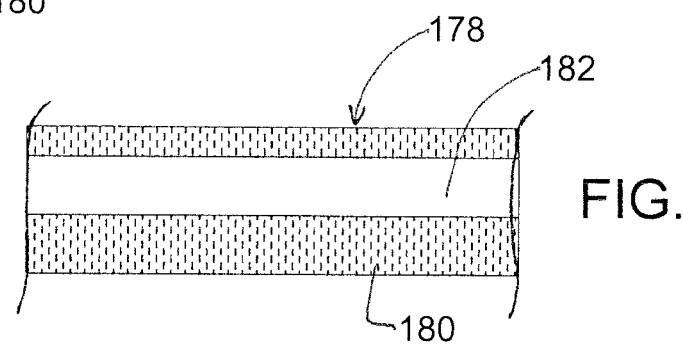

FIGS. 11-14 illustrate several embodiments that implement an intermittent pattern of discrete second metal regions 182, each in the context of a single filament 178 that can form one side of a cell 116 wherein (for example) four filaments 178 border some or all cells 116. One, some or all of the filaments bordering a cell 116 can have any of the patterns shown in FIGS. 11-14, or other intermittent pattern (s). FIG. 11 shows a pattern in which second metal regions 182 in the form of circular disks, polygons or other shapes are distributed in a (regular or random) spotted pattern in the first metal region 180. The disks, polygons, etc. can be of uniform or non-uniform size and/or shape. FIG. 12 shows a single second metal region 182 in the shape of a ring or band that can extend partially or completely around a filament 178. FIG. 13 shows a pattern that is similar to that of FIG. 12 but with multiple such rings or bands. FIG. 14 shows a pattern in which the second metal region 182 can take the form of one or more strips that extend longitudinally along the filament 178. Generally, the thickness of the second metal can be adjusted to increase or decrease the duration of the galvanic reaction.

In some embodiments, the second metal 182 can prevail in or cover some or all of the portion of the outer surface of the endovascular device, engagement member or expandable member 102 that faces radially outward, away from the central longitudinal axis of the endovascular device, engagement member or expandable member 102. For example, the second metal 182 can cover most or substantially all of such outward-facing surface of the expandable member 102, or most or substantially all of such outward-facing surface of the mesh, the distal portion 176, and/or the proximal portion 122. In various embodiments, the second metal can cover at least 50%, at least 60%, at least 75%, at least 90%, at least 95%, or at least 98% of any such outward-facing surface of the expandable member 102, the mesh, the distal portion 176, and/or the proximal portion 122. Additionally or alternatively, substantially all of such outward-facing surface of the expandable member 102 (or of the mesh, the distal portion 176, and/or the proximal portion 128) can be covered collectively by the second metal 182 in some areas and by some material other than the first metal 180 in other areas. In combination with any of the foregoing, the first metal 180 can cover, prevail in or be exposed in some or all of the portion of the outer surface of the expandable member 102 that faces radially inward, toward the central longitudinal axis of the expandable member 102 (or some or all of such inward-facing surface of the mesh, the distal portion 176, or the proximal portion 122). In the embodiments under discussion in this paragraph, the first metal can prevail substantially only on the inward-facing surface, and the second metal can prevail substantially only on the outward-facing surface, of the expandable member 102, the mesh, distal portion 176, or proximal portion 122. In some embodiments, at least 50%, at least 60%, at least 75%, at least 90%, at least 95%, or at least 98% of a total surface area of the second metal can be at the outward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the first metal can be at the inward-facing surface of the expandable member 102, the mesh, the distal portion 176, and/or the proximal portion 122. In some embodiments, the first metal can be substantially absent from the outward-facing surface, and/or the second metal can be substantially absent from the inward-facing surface, of the expandable member 102, the mesh, the distal portion 176 or proximal portion 122. In some embodiments, less than 50%, less than 40%, less than 25%, less than 10%, less than 5%, or less than 2% of a total surface area of the second metal can be at the inward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the second metal can be at other than the inward-facing surface of the expandable member 102, the mesh, the distal portion 176, and/or the proximal portion 122. In some embodiments, less than 50%, less than 40%, less than 25%, less than 10%, less than 5%, or less than 2% of a total surface area of the first metal can be at the outward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the first metal can be at the other than the outward-facing surface of the expandable member 102, the mesh, the distal portion 176, and/or the proximal portion 122.

In some embodiments, the second metal 182 can prevail in or cover some or all of the portion of the outer surface of the endovascular device, engagement member or expandable member 102 that faces radially inward, away from the central longitudinal axis of the endovascular device, engagement member or expandable member 102. For example, the second metal 182 can cover most or substantially all of such inward-facing surface of the expandable member 102, or most or substantially all of such inward-facing surface of the mesh, the distal portion 176, and/or the proximal portion 122. In various embodiments, the second metal can cover at least 50%, at least 60%, at least 75%, at least 90%, at least 95%, or at least 98% of any such inward-facing surface of the expandable member 102, the mesh, the distal portion 176, and/or the proximal portion 122. Additionally or alternatively, substantially all of such inward-facing surface of the expandable member 102 (or of the mesh, the distal portion 176, and/or the proximal portion 128) can be covered collectively by the second metal 182 in some areas and by some material other than the first metal 180 in other areas.

In combination with any of the foregoing, the first metal 180 can cover, prevail in or be exposed in some or all of the portion of the outer surface of the expandable member 102 that faces radially outward, toward the central longitudinal axis of the expandable member 102 (or some or all of such outward-facing surface of the mesh, the distal portion 176, or the proximal portion 122). In some of the embodiments under discussion in this paragraph, the first metal can prevail substantially only on the outward-facing surface, and the second metal can prevail substantially only on the inward-facing surface, of the expandable member 102, the mesh, distal portion 176, or proximal portion 122. In some embodiments, at least 50%, at least 60%, at least 75%, at least 90%, at least 95%, or at least 98% of a total surface area of the second metal can be at the inward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the first metal can be at the outward-facing surface of the expandable member 102, the mesh, the distal portion 176, and/or the proximal portion 122. In some embodiments, the first metal can be substantially absent from the inward-facing surface, and/or the second metal can be substantially absent from the outward-facing surface, of the expandable member 102, the mesh, the distal portion 176 or proximal portion 122. In some embodiments, less than 50%, less than 40%, less than 25%, less than 10%, less than 5%, or less than 2% of a total surface area of the second metal can be at the outward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the second metal can be at other than the outward-facing surface of the expandable member 102, the mesh, the distal portion 176, and/or the proximal portion 122. In some embodiments, less than 50%, less than 40%, less than 25%, less than 10%, less than 5%, or less than 2% of a total surface area of the first metal can be at the inward-facing surface of the expandable member 102, the mesh, the distal portion 176, and/or the proximal portion 122. In some embodiments, at least 50%, at least 60%, at least 75%, at least 90%, at least 95%, or at least 98% of a total surface area of the first metal can be at the other than the inward-facing surface of the expandable member 102, the mesh, the distal portion 176, and/or the proximal portion 122.

The endovascular device, engagement member or expandable member 102 (or mesh, or distal portion 176, or proximal portion 122) can have an outward-facing surface that is purely or substantially purely cathodic or anodic, and an inward-facing surface that is purely or substantially of the opposite polarity. In some such embodiments, the outward-facing surface is purely or substantially purely anodic and the inward-facing surface is purely or substantially purely cathodic, by employing a second metal of, e.g., zinc or magnesium that covers all or substantially all of the outward-facing surface and a first metal of, e.g., nitinol that covers all or substantially all of the inward-facing surface. In some such embodiments, the inward-facing surface is purely or substantially purely anodic and the outward-facing surface is purely or substantially purely cathodic, by employing a second metal of, e.g., zinc or magnesium that covers all or substantially all of the inward-facing surface and a first metal of, e.g., nitinol that covers all or substantially all of the outward-facing surface. The first metal can comprise the structural metal of the endovascular device, engagement member or expandable member 102, mesh, distal portion 176, or proximal portion 122. It may be useful to provide an outward-facing surface that is purely or substantially purely anodic, for example, to attract positively-charged thrombus and cause it to adhere to the outward-facing surface, where the thrombus may more likely to detach from the endovascular device, engagement member or expandable member 102 during removal (in contrast to the interior of the expandable member). It may be useful to provide an inward-facing surface that is purely or substantially purely anodic, for example, to attract positively-charged thrombus and cause it to adhere to the inward-facing surface and/or to avoid attachment to the vessel wall.

As depicted in FIGS. 1 and 2, some or all of the cells 116 can be open (e.g., uncovered) which can be useful when using the expandable member 102 for thrombectomy. Separately or additionally, the expandable member 102 as a whole, or the distal portion 176, can be uncovered. Some or all of the portion of the outer surface of the expandable member 102 that faces radially outward, away from the central longitudinal axis of the expandable member 102, can be uncovered such that the radially-outward-facing portion of the outer surface of the expandable member 102 can comprise, in whole or in part, a vessel-wall-contacting, catheter-contacting, or thrombus-contacting surface. In some embodiments, such a vessel-wall-contacting catheter-contacting, or thrombus-contacting surface can be partially or entirely metallic, comprising metals of the galvanic cell, for example one or both of the first metal 180 and the second metal 182. In some embodiments, such a vessel-wall-contacting, catheter-contacting, or thrombus-contacting surface can be substantially or entirely free of one or more metals of the galvanic cell, for example one or both of cathodic metal (e.g., the first metal 180) or anodic metal (e.g., the second metal 182). In some embodiments, less than 50%, less than 40%, less than 25%, less than 10%, less than 5%, or less than 2% of a total surface area of the second metal can be at the vessel-wall-contacting, catheter-contacting, or thrombus-contacting surface. In some embodiments, less than 50%, less than 40%, less than 25%, less than 10%, less than 5%, or less than 2% of a total surface area of the first metal can be at the vessel-wall-contacting, catheter-contacting, or thrombus-contacting surface. It may be useful to provide an outward-facing surface or a vessel-wall-contacting catheter-contacting, or thrombus-contacting surface that is substantially or entirely free of anodic metal (i) to facilitate delivery and retrieval by providing a lower displacement force between the expandable member 102 (or a portion thereof) and a catheter, as compared to a force that would be required if the an outward-facing surface or a vessel-wall-contacting catheter-contacting, or thrombus-contacting surface comprised anodic metal, (ii) to protect the anodic metal from disruption, e.g., shearing, that might occur from sliding contact between the anodic metal and the catheter, or both.

As discussed above, the expandable member 102 can comprise overlap zones 128 in some embodiments. In some such embodiments, the outer surface of the expandable member in the overlap zones that would contact each other in a volume-reduce form in a catheter or during transition between the volume-reduced form and expanded configurations are substantially or entirely free of anodic metal. This may (i) facilitate delivery and retrieval by diminishing friction that may impede the expansion or contraction of the expandable member (or portion thereof), (ii) to protect the anodic metal from disruption, e.g., shearing, that might occur from sliding contact between portions of the outer surface in the overlap zones 128, or both.

Figure 19:
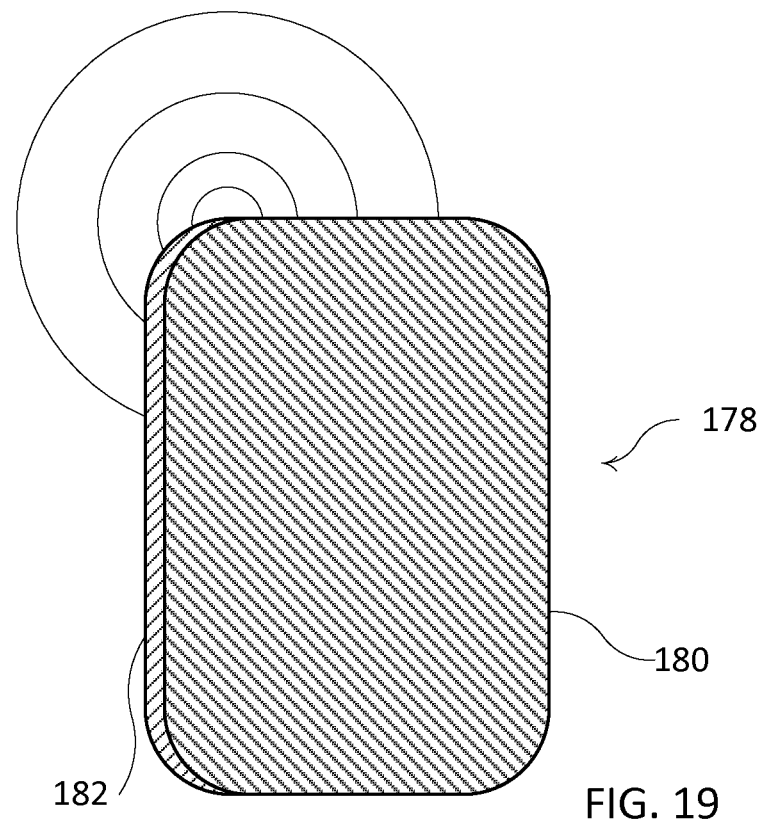
Figure 20:
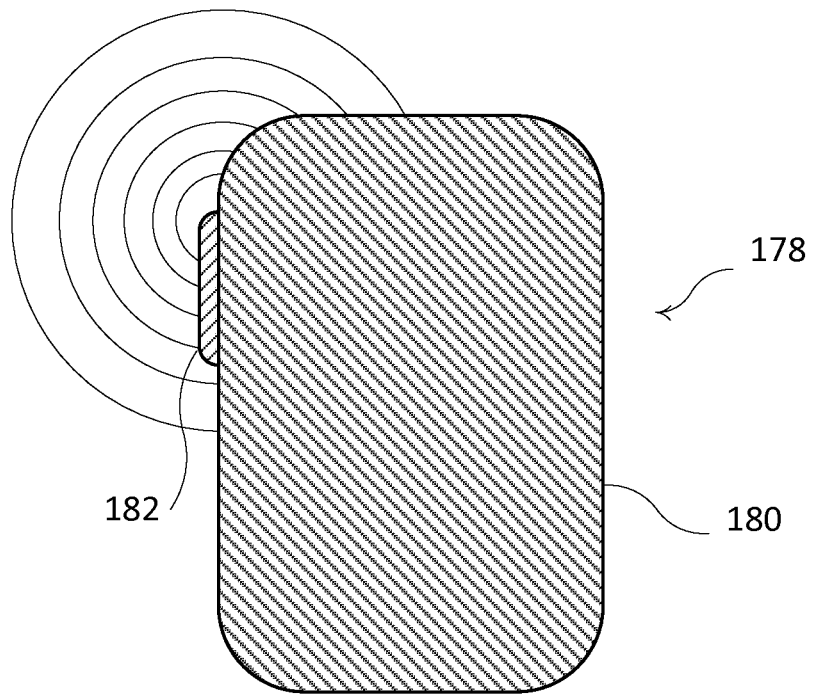

The ratio of anode surface area to cathode surface area affects the density of the generated current and the rate of the galvanic reaction. As the area of the anode becomes smaller compared to the cathode area, the current density increases and the reaction rate increases. Consider, for example, the filaments 178 shown in schematic cross-sections in FIGS. 19 and 20. As the galvanic cell of FIG. 19 has a higher ratio of anodic to cathodic surface area, it would generate a lower charge density and have a slower corrosion rate in the galvanic cell of FIG. 20. In a galvanic cell of the expandable member 102, the anodic metal can form from about 35% or about 45% to about 75% or about 85% of a total surface area of the galvanic cell. In the galvanic cells of some embodiments, the anodic metal can form about 35%, about 45%, about 55%, about 65%, about 75%, or about 85% of a total surface area of the galvanic cell.

The thickness of the anode affects the total reaction time of the galvanic cell. In some embodiments, the thickness of the anode is selected to provide 5-10, 15-20, or 20-25 minutes of reaction time. In further embodiments, the thickness of the anode can be selected to provide 5-10 minutes of reaction time after positioning the expandable member 102 in a blood vessel. In some embodiments wherein the anode comprises magnesium and the cathode comprises nitinol, a magnesium thickness of about 2 to 3 micrometers can provide at least about five minutes of reaction time, e.g. where the anode:cathode area ratio is about 1:1. The thickness of the anodic metal may vary over a region of its coverage. For example, when the anodic metal is applied to a structural material by vapor deposition, the anodic metal may be thicker, as measured in a direction normal to the receiving surface, in regions oriented directly toward the direction of deposition than other regions.

Some or all of the expandable member 102 can be covered by a thin, dissolvable covering 188 (see FIGS. 16 and 18), e.g., film, that delays electrical activity of the galvanic cell until an amount of time has passed in the presence of a solvent, which may be a constituent of blood. For example, a dissolvable covering can isolate the implant from the blood until it dissolves, allowing the user to position or otherwise manipulate the expandable member before a galvanic reaction occurs. The dissolvable covering can cover some or all of the mesh, the proximal portion 122, the distal portion 176, the contacting portion of the outer surface of the expandable member in the overlap zones, or a combination thereof. The film can comprise a bioabsorbable polymer, for example, polylactic or polyglycolic acid, or a sugar, wax, oil, etc. The dissolvable covering can have a low coefficient of friction of contact with itself and a material forming an inner wall of a catheter, to facilitate delivery and deployment of the expandable member.

Figure 21A:
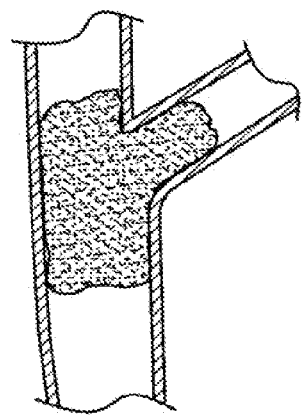
FIGS. 21A-21D schematically illustrate thrombi located in various vessel arrangements.
Figure 21B:
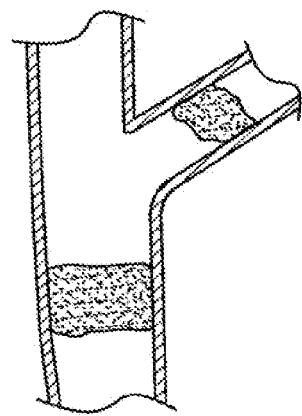
Figure 21C:
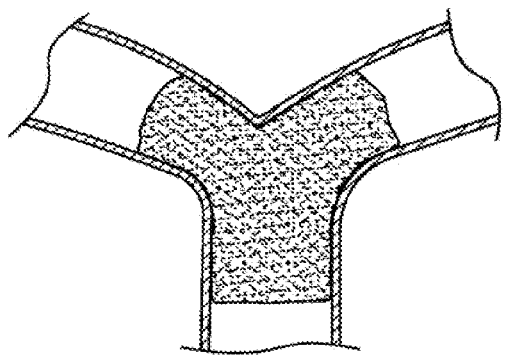
Figure 21D:
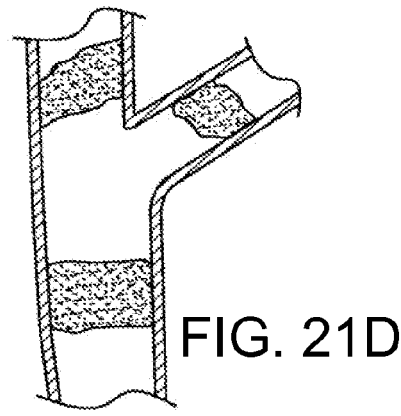

Referring to FIGS. 21A-D, in some embodiments the expandable member 102 can be used as a flow restoration device and/or an implantable member (e.g. stent) in a vessel, including at bifurcation, bi-vessel, and/or multi-vessel locations in mammalian vasculature, e.g. in the neurovasculature or in the peripheral vasculature. For example, and with reference to FIG. 21A, thrombi can be located at bifurcations in the neurovasculature such as the internal carotid artery and the anterior cerebral artery, or internal carotid artery and middle cerebral artery, or the basilar artery and the posterior cerebral artery. With reference to FIG. 21B, thrombi can also be located at two vessels (i.e. bi-vessels) as two separate clots in similar vessels. With reference to FIGS. 21C and 21D, thrombi can also be located at multi-vessels as one clot that is within multiple vessels or as multiple clots that are within multiple vessels. Vessels with such clots can be located, for example, at the intracranial internal carotid, anterior cerebral and middle cerebral arteries, and basilar artery and both posterior and cerebral arteries, or in the peripheral vasculature, such as the deep venous system of the legs when treating deep vein thrombosis.

Figure 22:
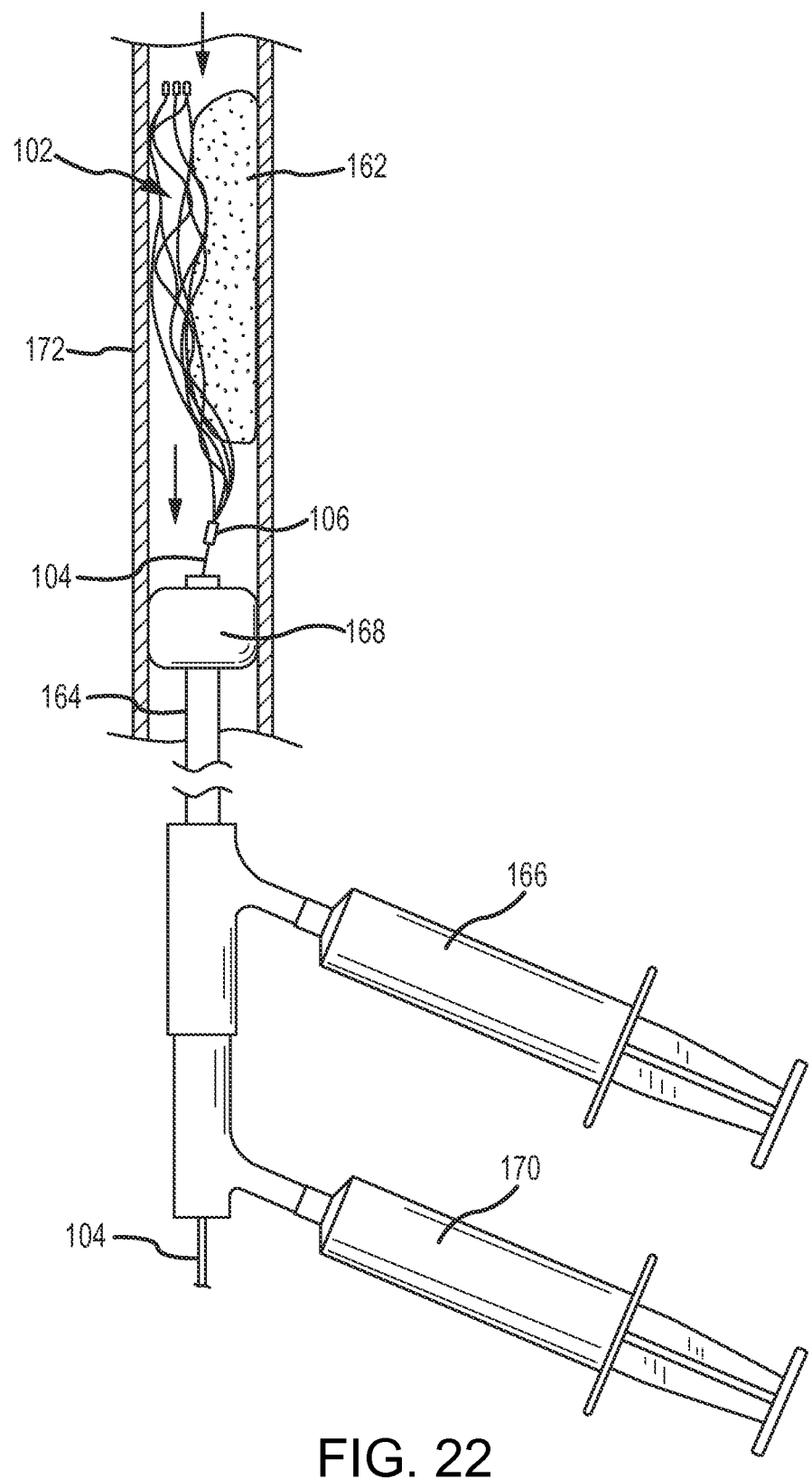
FIG. 22 schematically illustrates a system for blood flow restoration, thrombus removal, or both.

Referring to FIG. 22, the medical device 100 can be used in a system with a balloon guide catheter 164, with a syringe 166 for expanding a balloon 168, a syringe 170 for aspiration, or both. Aspiration assistance can enable flow reversal through the expandable member 102 and thrombus 162. Inflation of the balloon 168 can impede or prevent flow proximally through the vessel from the balloon 168 towards the expandable member 102. As part of the retrieval procedure, continuous aspiration can be employed through the balloon guide catheter 164, with vigorous aspiration when the expandable member 102 is near a distal tip of the balloon guide catheter. The aspiration with flow reversal can help allow the distal vasculature to continue to have blood perfusing through the vessels during the retrieval process, and can inhibit the possibility of distal emboli. There can be an advantage to having blood flow across the expandable member 102 and thrombus 162 with the potential of natural lysing of blood and increased surface area for thrombus dissolving medicines, if they are provided. The aspiration with flow reversal can also assist in the thrombus retrieval process by aiding in the removal of the thrombus 162. The flow can be directed towards a lumen of the balloon guide catheter 164 due to the aspiration. The expandable member 102 and thrombus 162 can thus be assisted by the flow to enter the lumen of the balloon guide catheter 164. In some embodiments, if withdrawal into the balloon guide catheter 164 is difficult for any reason during aspiration, the balloon 168 can be deflated, and the balloon guide catheter 164, catheter 107, and expandable member 102 can be withdrawn simultaneously while maintaining aspiration.

Figure 23:
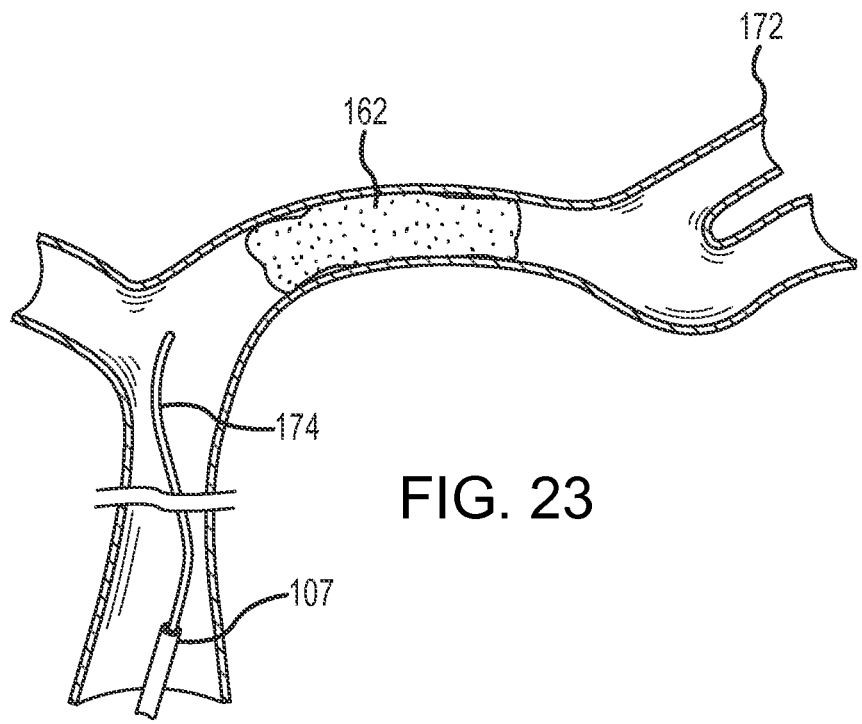
FIGS. 23-32 are cross-sectional views of a vessel and illustrate use of a device according to some embodiments.
Figure 24:
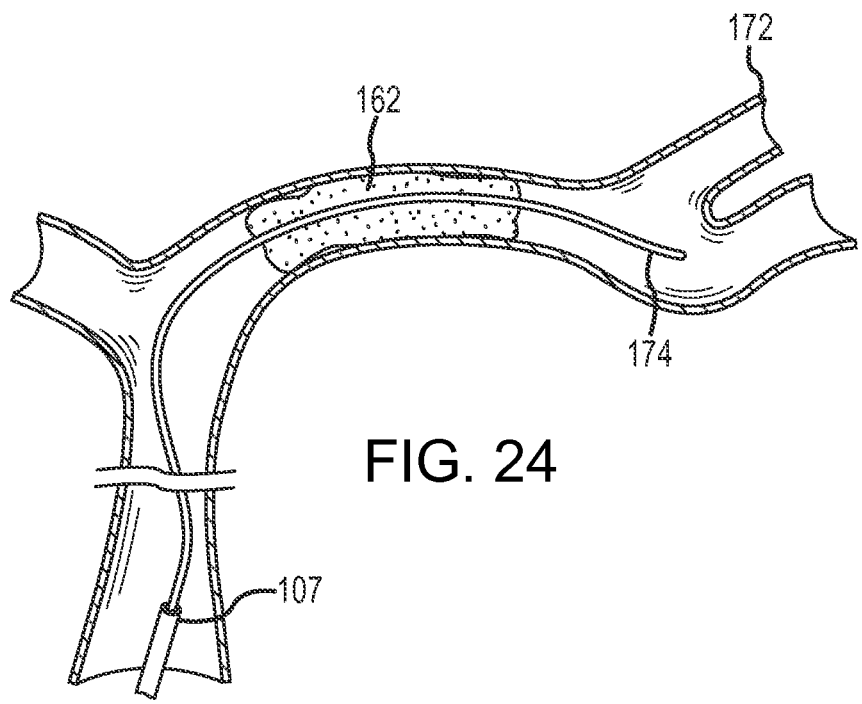
Figure 25:
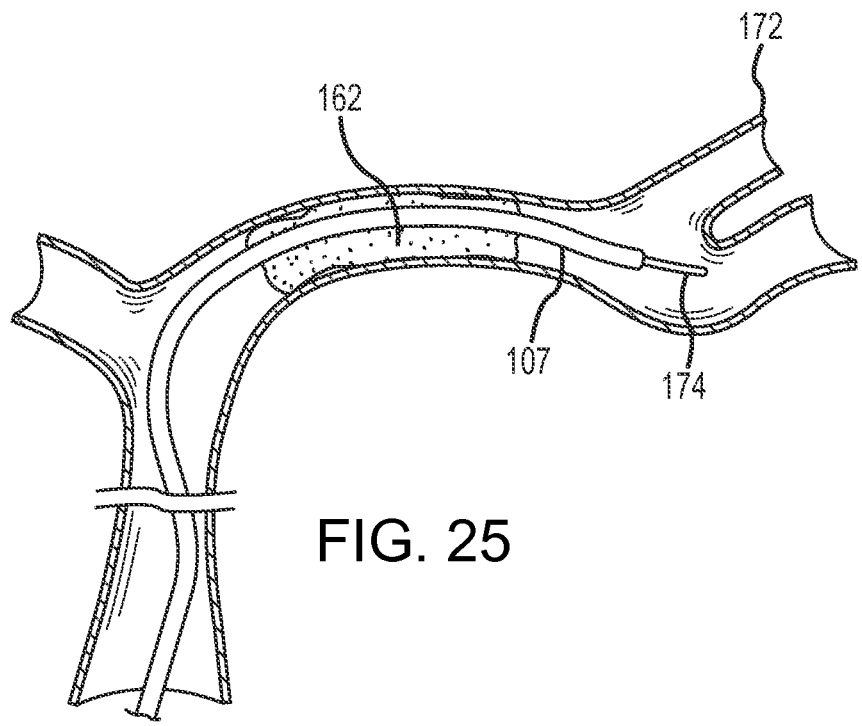

A technique for engaging and removing a thrombus 162 and restricting downstream travel of secondary emboli during thrombus retrieval will now be discussed with reference to FIGS. 23-32. This technique can be performed with any of the embodiments of the medical device 100 and expandable member 102 disclosed herein, including any of the expandable members 102 of FIG. 2, 8, 9 or 10. Referring to FIG. 23, the medical device 100 may be inserted into an anatomical vessel 172 by first inserting a guide wire 174 into the anatomical vessel 172. The guide wire 174 is advanced through a guide catheter 164, which optionally includes a balloon near the guide catheter's distal end, and a catheter 107 to the treatment site, adjacent the thrombus 162. Referring to FIG. 24, the guide wire 174 is advanced distally through the thrombus 162. Once in position, the catheter 107 is advanced over the guide wire 174, through a distal end of the guide catheter, into the anatomical vessel 172. Referring to FIG. 25, the catheter 107 is advanced distally through the thrombus 162. The guide wire 174 is then withdrawn proximally.

Figure 26:
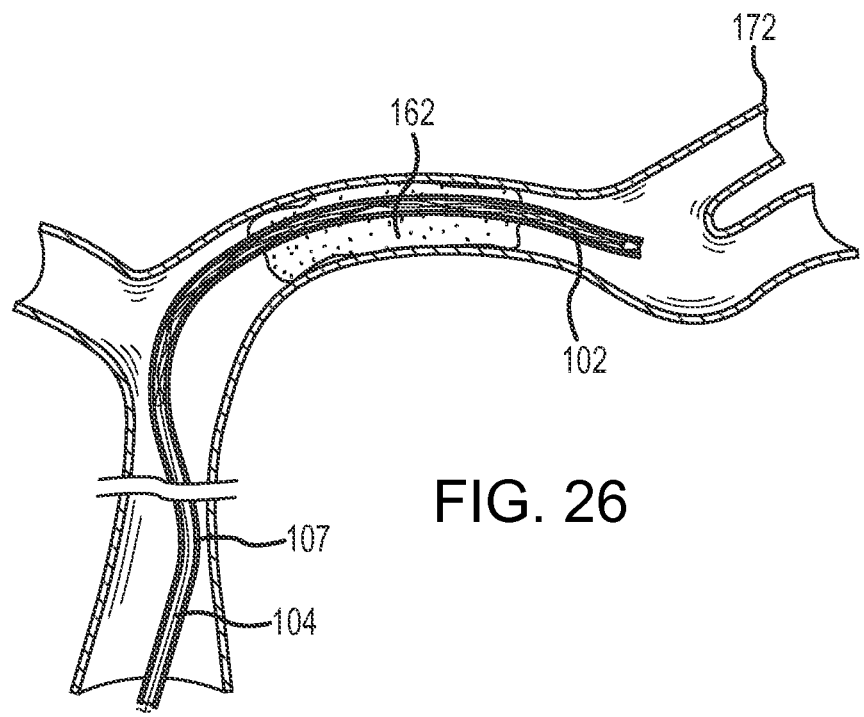

Referring to FIG. 26, the medical device 100 is advanced through the catheter 107 such that the distal portion 120 of the medical device 100 is disposed distal of the thrombus 162 in the anatomical vessel 172. The medical device 100 is advanced through the catheter 107 by the manipulation member 104 coupled to the proximal end of the expandable member 102. The catheter 107 compresses the expandable member 102 and thus, maintains the expandable member 102 in a compressed, volume-reduced configuration as the expandable member 102 is advanced to the treatment site.

Figure 27:
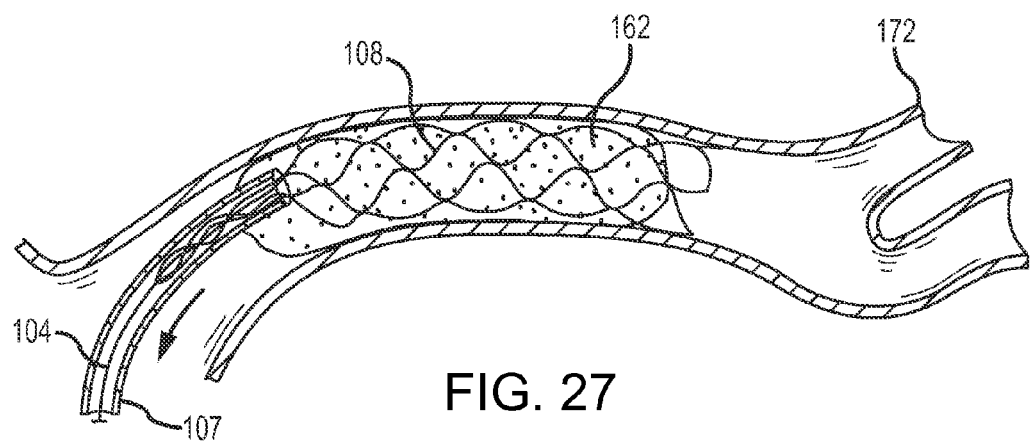
Figure 28:
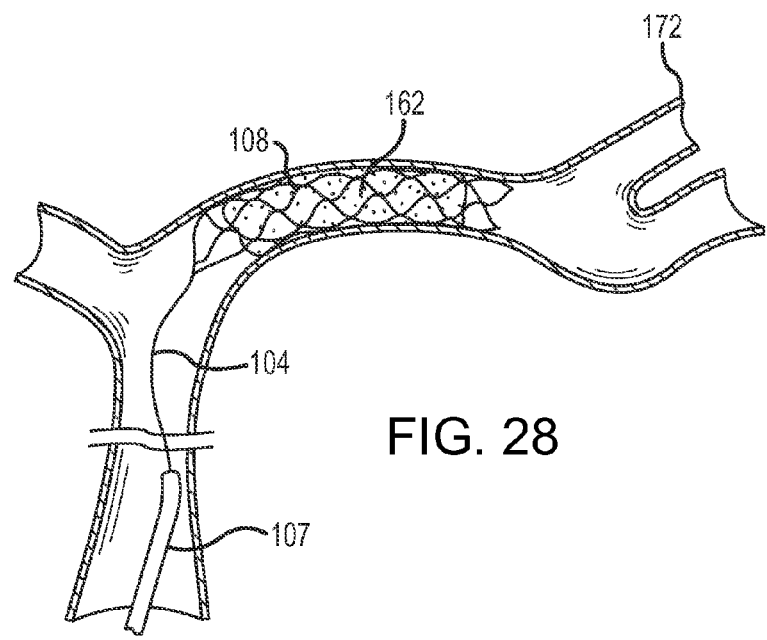

Referring to FIGS. 27 and 28, the catheter 107 is withdrawn proximally relative to the expandable member 102 to expose the expandable member 102. If the expandable member is self-expanding, retraction of the catheter 107 can permit the expandable member 102 to expand. The frame 108 expands against a length of the thrombus 162 and engages the thrombus 162. As discussed above, the frame 108 is designed to engage and remove thrombi that are both generally soft, or malleable, or generally hard, or callous. A period of time can be allowed to pass to allow blood to reperfuse the downstream area, the expandable member 102 to penetrate the thrombus 162, or both.

Once the expandable member 102 has been expanded into the thrombus 162, the expandable member 102 can grip the thrombus, by virtue of its ability to mechanically interlock with the thrombus as well as its ability to electrically attract, adhere, and/or attach to the thrombus 162. The galvanic cell(s) and/or region(s) can begin a galvanic reaction before or after the expandable member 102 has been released from the catheter 107 into the anatomical vessel 172 (e.g., an intracranial vessel) and/or expanded into the thrombus 162. The expandable member 102 can be left in place or manipulated within the vessel for a time period while the galvanic cell(s) and/or region(s) are reacting. Any positively charged portions of the expandable member 102 can attract negatively charged constituents of the thrombus 162, and any negatively charged portions of the expandable member 102 can attract positively charged constituents of the thrombus 162, thereby enhancing the grip of the expandable member 102 on the thrombus 162. This allows the expandable member 102 to be used to retrieve the thrombus 162 (discussed below) with reduced risk of losing grip on the thrombus or a piece thereof, which can migrate downstream and cause additional vessel blockages in areas of the brain that are more difficult to reach. These advantages can be achieved via the galvanic cell(s) and/or region(s) discussed herein, without need for a separate, extracorporeal voltage source, wires, or other conductors extending from the source to the expandable member 102, or switches or other controls regulating the application of voltage.

In some embodiments, at least a portion of the thrombus 162 is attracted, adhered, and/or attached to an inwardly facing surface of the expandable member 102. Blood constituents can be bound primarily or substantially only to an inwardly facing surface of the mesh in some embodiments.

Figure 29:
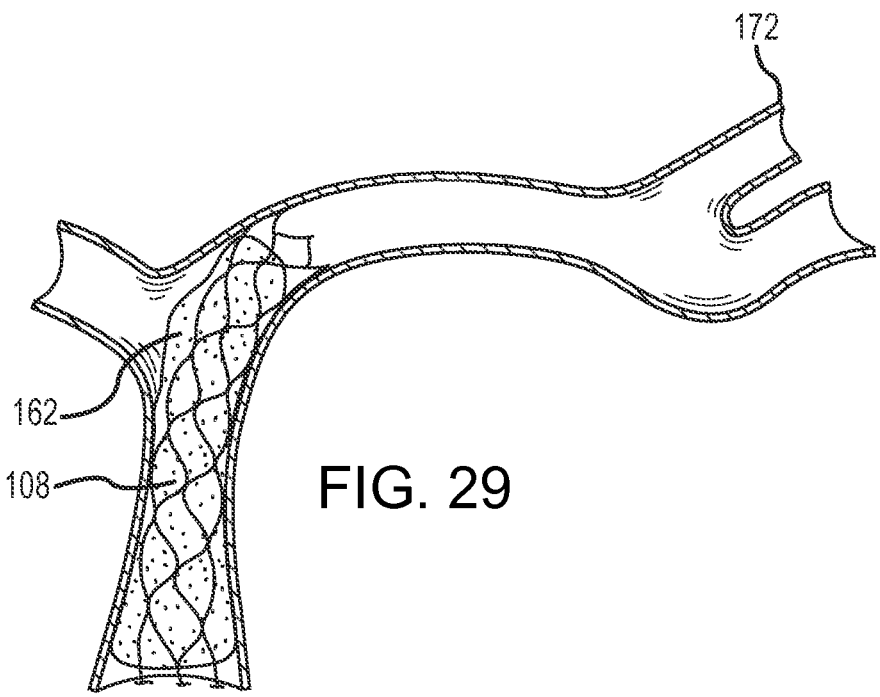
Figure 30:
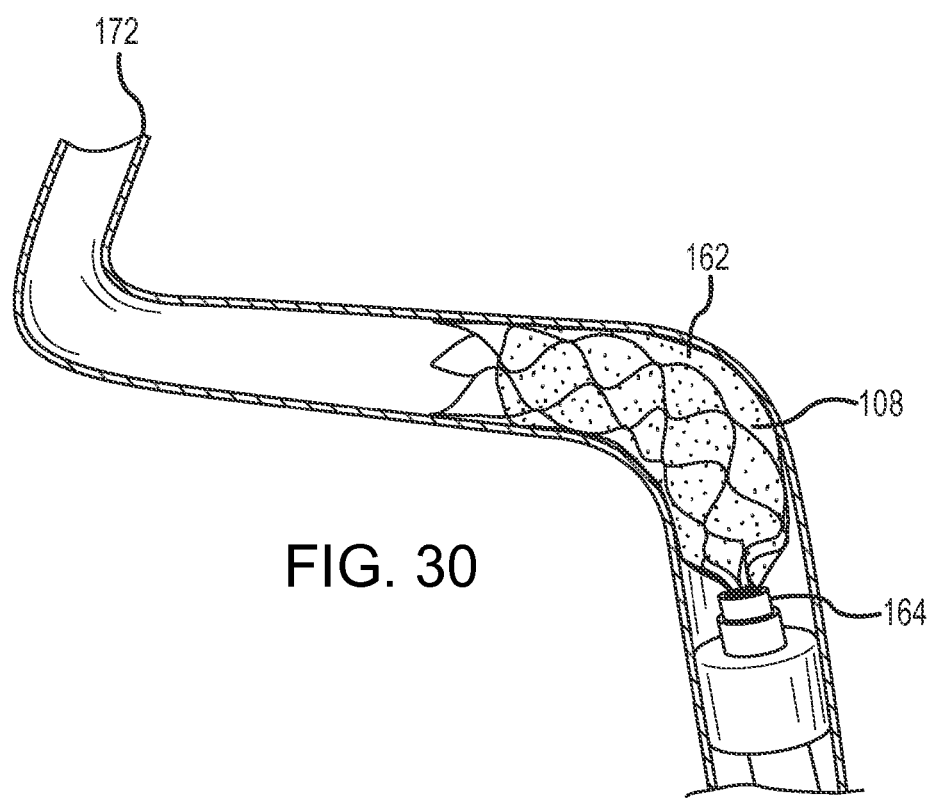
Figure 31:
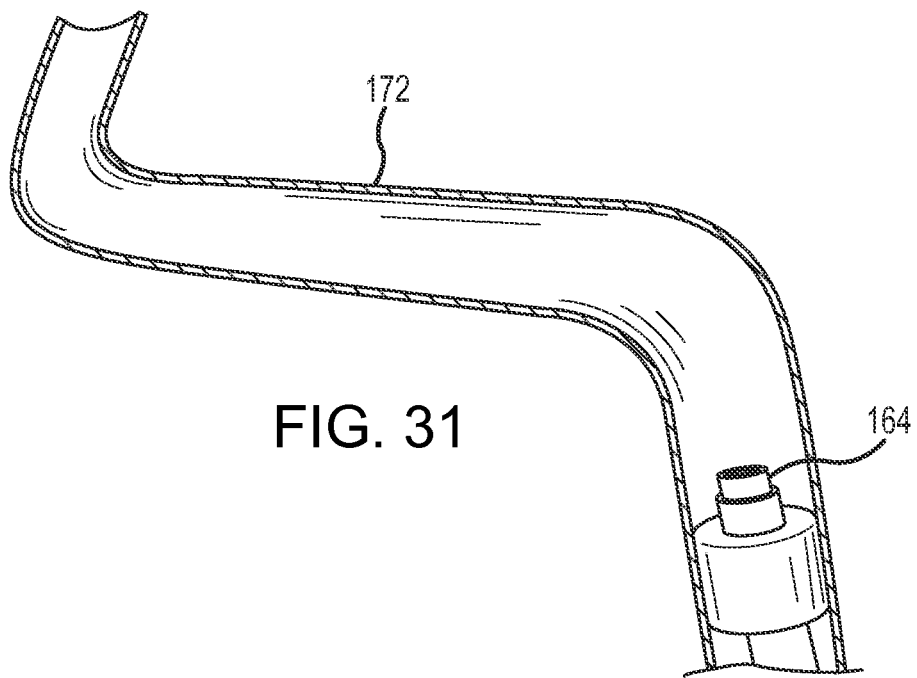

With reference to FIGS. 29-31, once the endovascular expandable member 102 has engaged and captured the thrombus 162, the thrombus 162 can be removed. For example, the expandable member 102 with the thrombus 162 gripped thereby, can be retracted (for example, along with the microcatheter 108) proximally toward the balloon guide catheter. During this retraction, the expandable member 102 can grip the thrombus 162 electrostatically, e.g., via the galvanic cell(s) and/or region(s) discussed herein. Accordingly, the expandable member 102 can maintain an enhanced or electrostatically-enhanced grip on the thrombus 162 during retraction. The expandable member 102 and thrombus therefore form a removable, integrated thrombus-device mass wherein the connection of the thrombus to the device is electrostatically enhanced, e.g. via the galvanic cell(s) and/or region(s) discussed herein.

Prior to retracting the expandable member 102 and thrombus 162, the catheter 107 or the guide catheter 164 can be manipulated. For example, the catheter 107 or the guide catheter 164 can be moved forward to a predetermined point relative to the expandable member 102. Use of markers along the catheter 107, or the guide catheter 164, and/or expandable member 102 can be used to determine the relative locations of the catheter 107, the guide catheter 164, and expandable member 102. Description of the use of such markers can be found, for example, in PCT Publication No. WO 2009/105710, which is incorporated by reference in its entirety.

Referring to FIGS. 29 and 30, the expandable member 102 is withdrawn proximally, along with the thrombus 162. Applying a proximally directed force to a proximal end of the frame 108 can collapse a distal end of the frame 108, prior to withdrawal of the intervention member into the guide catheter 164. The distal end of the frame 108 can collapse to at least substantially the same extent, and optionally more than, a portion of the frame proximal of the distal end as discussed above.

Referring to FIGS. 22, 30, and 31, in embodiments wherein the guide catheter 164 comprises a balloon 168, the balloon optionally can be inflated to occlude flow during retraction of the thrombus 162 toward the guide catheter. In some embodiments, an aspiration syringe 170 can be attached to the guide catheter 164, and aspiration can be applied to aid thrombus retrieval.

Figure 32:
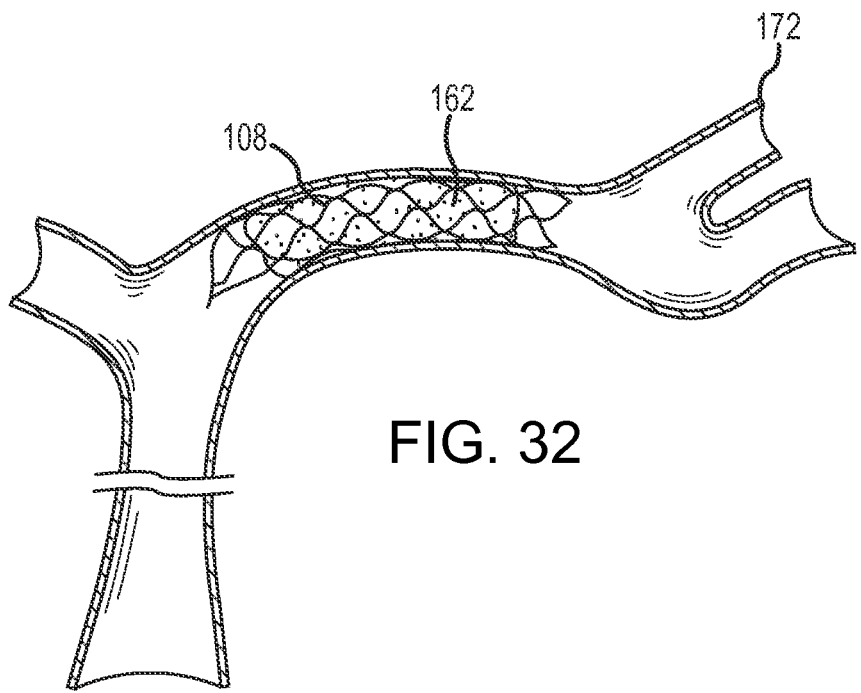

Referring to FIG. 31, the expandable member 102 is withdrawn proximally to the guide catheter 164. The guide catheter 164 causes the frame 108 to collapse, with the thrombus 162 engaged therein. The thrombus 162 is thus retrieved and removed from the anatomical vessel 172. Referring to FIG. 32, if retrieval of the expandable member 102 is determined to be undesirable, e.g., to avoid damaging the vessel 172, and the expandable member 102 is detachably connected to the manipulation member 104, the expandable member can be detached from the manipulation member 104 and can remain in the vessel 172.

Additionally, while the expandable member 102 described above has been described in the context of use during a blood flow restoration procedure, the expandable member 102 can also, or alternatively, be used as an implantable member (e.g. stent). For example, the expandable member 102 can be released through the connection 106 at a stenosis, aneurysm, or other appropriate location in a vessel. The expandable member 102 can expand and engage a vessel wall so as to hold the vessel wall open and/or act as an occluding member. While the filament thicknesses, widths, cell sizes, and forces described above can be optimized for an expandable member 102 for flow restoration, these values can also be optimized for an expandable member 102 for use as an implantable member. In some embodiments the same values can be used for both flow restoration and use as an implantable member.

Further details regarding expandable members, the manufacture of expandable members, and use of expandable members are disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. Patent Publication No. 2014/0194919, entitled Connection of an Endovascular Intervention Device to a Manipulation Member, published on Jul. 10, 2014; and U.S. Patent Publication No. 2014/0194911, entitled Connection of a Manipulation Member, Including a Bend without Substantial Surface Cracks, to an Endovascular Intervention Device, published on Jul. 20, 2014; and U.S. patent application Ser. No. 14/026,302, entitled Endovascular Device Engagement, filed on Sep. 13, 2013; the entirety of each of which is hereby incorporated by reference herein.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medical device configured to perform an endovascular therapy, the device comprising:
   an elongate manipulation member comprising a distal end portion; and
   an intervention member comprising a proximal end portion and a mesh, the proximal end portion being coupled with the distal end portion of the elongate manipulation member, the mesh having a plurality of cells in a tubular configuration and being compressible to a collapsed configuration for delivery to an endovascular treatment site through a catheter and being self-expandable from the collapsed configuration to an expanded configuration, and the mesh comprising an anodic metal and a cathodic metal, and the anodic metal and the cathodic metal each forming a fraction of a total surface area of the mesh, wherein an inwardly facing surface of the mesh is formed substantially only by the anodic metal, and an outwardly facing surface of the mesh is formed substantially only by the cathodic metal.

2. The medical device of claim 1, wherein the fraction of the surface area formed by the anodic metal comprises a plurality of discrete portions of the anodic metal.

3. The medical device of claim 1, wherein the fraction of the surface area formed by the anodic metal is contiguous.

4. The medical device of claim 1, wherein an engagement portion of the surface area is configured to engage an interior surface of a catheter during delivery of the medical device through a lumen of the catheter, and an average coefficient of friction of the engagement portion is less than an average coefficient of friction of the surface area excluding the engagement portion.

5. The medical device of claim 1, wherein an engagement portion of the surface area is configured to engage an interior surface of a catheter during delivery of the medical device through a lumen of the catheter, and substantially none of the engagement portion is formed by the anodic metal.

6. The medical device of claim 1, wherein the anodic metal is in direct contact with the cathodic metal.

7. The medical device of claim 1, wherein at least a portion of the anodic metal has a thickness of at least 2 µm.

8. The medical device of claim 1, wherein the anodic metal comprises magnesium and the cathodic metal comprises nickel and titanium.

9. The medical device of claim 1, wherein the mesh is rolled in the collapsed configuration such that a first portion and a second portion of the mesh are overlapped in at least one radial direction with a surface area of the first portion contacting a surface area of the second portion, and each of the surface area of the first portion and the surface area of the second portion comprises substantially no anodic metal.

10. The medical device of claim 1, further comprising a temporary cover material that encapsulates at least a portion of the anodic metal.

11. The medical device of claim 10, wherein the temporary cover material is erodible, dissolvable, degradable or absorbable in vivo.

12. The medical device of claim 11, wherein the temporary cover material encapsulates substantially all of the anodic metal.

13. A medical device configured to perform an endovascular therapy, the device comprising:
   an elongate manipulation member comprising a distal end portion; and
   an intervention member comprising a proximal end portion and a mesh, the proximal end portion being coupled with the distal end portion of the elongate manipulation member, the mesh having a plurality of cells in a tubular configuration and being compressible to a collapsed configuration for delivery to an endovascular treatment site through a catheter and being self-expandable from the collapsed configuration to an expanded configuration, and the mesh comprising means for galvanically assisting internal attachment of the mesh to thrombus, wherein an inwardly facing surface of the mesh is formed substantially only by an anodic metal, and an outwardly facing surface of the mesh is formed substantially only by a cathodic metal.

14. The medical device of claim 13, wherein the means for galvanically assisting attachment of the mesh to thrombus comprises the anodic metal and the cathodic metal.

15. The medical device of claim 13, wherein the anodic metal comprises magnesium and the cathodic metal comprises nickel and titanium.

* * * * *